United States Patent
Nguyen

(10) Patent No.: US 10,127,825 B1
(45) Date of Patent: Nov. 13, 2018

(54) APPARATUS, METHOD, AND SYSTEM OF INSIGHT-BASED COGNITIVE ASSISTANT FOR ENHANCING USER'S EXPERTISE IN LEARNING, REVIEW, REHEARSAL, AND MEMORIZATION

(71) Applicant: FUVI COGNITIVE NETWORK CORP., Framingham, MA (US)

(72) Inventor: Phu-Vinh Nguyen, Sherborn, MA (US)

(73) Assignee: FUVI COGNITIVE NETWORK CORP., Framingham, MA (US)

( * ) Notice: Subject to any disclaimer, the term of this patent is extended or adjusted under 35 U.S.C. 154(b) by 0 days.

(21) Appl. No.: 15/870,210

(22) Filed: Jan. 12, 2018

Related U.S. Application Data

(60) Provisional application No. 62/518,824, filed on Jun. 13, 2017.

(51) Int. Cl.
*G09B 5/06* (2006.01)
*A61B 5/16* (2006.01)
*G10L 15/04* (2013.01)
*G10L 15/26* (2006.01)
*A61B 5/0476* (2006.01)
*G09B 19/02* (2006.01)

(52) U.S. Cl.
CPC ............ *G09B 5/065* (2013.01); *A61B 5/0476* (2013.01); *A61B 5/165* (2013.01); *G10L 15/04* (2013.01); *G10L 15/265* (2013.01); *G09B 19/025* (2013.01)

(58) Field of Classification Search
CPC ........... G09B 5/02; A61B 5/165; A61B 5/743; A61B 5/7425; A61B 2560/0475; G06K 9/78; G10L 25/63
See application file for complete search history.

(56) References Cited

U.S. PATENT DOCUMENTS

| | | | |
|---|---|---|---|
| 6,190,314 B1* | 2/2001 | Ark | A61B 5/16 463/36 |
| 9,355,110 B1* | 5/2016 | Chi | G02B 27/0172 |
| 9,711,056 B1 | 7/2017 | Nguyen | |
| 2002/0032689 A1* | 3/2002 | Abbott, III | G06F 17/30017 |
| 2010/0100546 A1* | 4/2010 | Kohler | G06F 17/30017 707/739 |
| 2013/0063550 A1* | 3/2013 | Ritchey | G03B 37/00 348/36 |

(Continued)

OTHER PUBLICATIONS

How We Learn Versus How We Think We Learn (https://youtu.be/oxZzoVp5jml) Web Based Video Published May 3, 2016.

(Continued)

*Primary Examiner* — Michael Grant
(74) *Attorney, Agent, or Firm* — Sughrue Mion, PLLC

(57) ABSTRACT

A personal intuition-based cognitive assistant system includes one or more components which may be worn by a user as a camera-headset, one or more sensors that capture an intuitive state of the user, a camera that capture videos, a processor that provides a cognitive navigating map for the captured videos based on the captured intuitive states of the user, and an inputter that input notes, comments to the videos linked by cognitive navigating map, and a memory to store all components of the information with links and identified cognitive map.

19 Claims, 21 Drawing Sheets

(56) References Cited

U.S. PATENT DOCUMENTS

| | | | | |
|---|---|---|---|---|
| 2013/0211238 | A1* | 8/2013 | DeCharms | A61B 5/4824<br>600/418 |
| 2014/0067730 | A1* | 3/2014 | Kozloski | G06N 7/005<br>706/12 |
| 2014/0323817 | A1* | 10/2014 | el Kaliouby | A61B 5/165<br>600/300 |
| 2014/0350349 | A1* | 11/2014 | Geurts | A61B 5/0022<br>600/300 |
| 2014/0351337 | A1* | 11/2014 | Pal | G09B 19/06<br>709/204 |
| 2015/0051451 | A1* | 2/2015 | Kido | G06F 19/28<br>600/301 |
| 2015/0052092 | A1* | 2/2015 | Tang | G06N 99/002<br>706/16 |
| 2015/0079560 | A1* | 3/2015 | Cowan | A61B 5/742<br>434/236 |
| 2015/0213002 | A1* | 7/2015 | Gou | G06F 17/2785<br>704/9 |
| 2015/0297108 | A1* | 10/2015 | Chase | G09B 5/00<br>600/9 |
| 2015/0297109 | A1* | 10/2015 | Garten | A61B 5/04845<br>600/544 |
| 2016/0042648 | A1* | 2/2016 | Kothuri | G06F 3/015<br>434/236 |
| 2016/0077547 | A1* | 3/2016 | Aimone | G06F 3/012<br>345/8 |
| 2016/0379106 | A1* | 12/2016 | Qi | G06N 5/04<br>706/11 |
| 2017/0007165 | A1* | 1/2017 | Jain | A61B 5/0478 |
| 2017/0236441 | A1* | 8/2017 | Chuang | G09B 11/00<br>434/236 |
| 2017/0351330 | A1* | 12/2017 | Gordon | A61B 5/0015 |
| 2018/0032126 | A1* | 2/2018 | Liu | G06F 3/011 |
| 2018/0032682 | A1* | 2/2018 | Donalds | G06F 19/322 |

OTHER PUBLICATIONS

Learning and Memory: How it Works and When it Fails (https://www.youtube.com/watch?v=a_HfSnQqeyY&t=1846s) Web Based Video Published Jun. 8, 2010.

The Neuroscience of Memory—Eleanor Maguire (https://youtu.be/gdzmNwTLakg) Web Based Video Published Mar. 13, 2014.

We are what we remember: memory and the biological basis of individuality (https://www.youtube.com/watch?v=skyvzMxtLu8&feature=youtu.be) Web Based Video Published Dec. 10, 2013.

Barbara Oakley: "Learning How to Learn" | Talks at Google (https://youtu.be/vd2dtkMINIw) Web Based Video Published Feb. 22, 2015.

The Power of a Mind to Map: Tony Buzan at TEDxSquareMile (https://www.youtube.com/watch?v=nMZCghZ1hB4&feature=youtu.be) Web based Video Published Dec. 18, 2012.

International Search Report and Written Opinion dated Jun. 15, 2018, issued by the International Searching Authority in counterpart International Patent Application No. PCT/US18/32516.

* cited by examiner

APPARATUS, METHOD, AND SYSTEM OF INSIGHT-BASED COGNITIVE ASSISTANT FOR ENHANCING USER'S EXPERTISE IN LEARNING, REVIEW, REHEARSAL, AND MEMORIZATION

CROSS REFERENCE TO RELATED APPLICATIONS

This application claims priority from U.S. Provisional Application No. 62/518,824 filed Jun. 13, 2017, the contents of which are incorporated herein by reference in its entirety.

BACKGROUND

1. Field

Apparatuses, methods, systems, and computer readable mediums consistent with exemplary embodiments broadly relate to cognitive technology, and more particularly, to learning and memory related technology.

2. Description of Related Art

Nowadays, the world's knowledge grows very quickly. Students are challenged with vast amounts of information from schools and other places. The vast amount of information is often presented to the student in a lecture format throughout the years of learning.

Research in the field of memory appears to shown that a person can retain very limited amount of sensory information in his or her short-term memory. Unless a segment of sensory information receives a cognitive processing task in a working memory of a person, it is forgotten in just a few seconds. This is particularly true when a person does not like a topic of the sensory information, a pain center in his or her brain is activated and causes a procrastination. A person in such situations tends to funnel his or her attention to more pleasant thoughts as opposed to studying the disliked topic. As a consequence, the learning results will be poor for this person.

Research also shows that a person can attain a more comprehensive understanding on a complex topic by navigating, scanning, correlating, and establishing chunks of information. A chunk includes a correlative net for several correlated features within the topic. And if each new established chunk is again correlated to other chunks in that topic and that person's insights, a fully comprehensive understanding on the topic is attained and a new long-term memory is well established in that person insights through an insight chunking network. See e.g., about procrastination, focused mode, diffused mode and chunking method in "Learning How to Learn," Barbara Oakley, https://youtu.be/vd2dtkMINIw, last visited on Jan. 7, 2018.

To apply the above method for today's learning technology, students can use cameras to take videos of their lectures during various classroom sessions during the day at school. Students can also take notes during the lecture into their notebooks or laptops. At home, they may play back the videos on screens or TV and then correlate the notes with corresponding episodes to review and rehearse the lecture from one point to another or from topic to topic as guided by the notes.

However, reviewing a long video, from beginning to an end may take a long time and many efforts. Furthermore, students are only able to take notes at time points or for topics that they understand and notes may be lost or confusing at the time points or on topics they are confused about or when they are disinterested.

When reviewing, it is not easy to track and put the notes, comments into the correlated specific episodes in the video. When saving the works, the links between notes, comments, and the correlated specific episodes are usually lost. Therefore, the effectiveness of learning process and the use of such saved information in future is limited.

The lecturer also has very limited feedback signals from their students to help him or her recognize the points or the time that his or her students are bored, sleepy, or confused and the time or points that are interesting and exciting for the students.

There is a need in the art to monitor, collect, and mark the cognitive states of a student or students onto and along their lecture so that they can navigate the necessary points to review. There is a need to add notes, sketches, and/or comments directly into the specific episodes of a video lecture. Additionally, there is a need to document a part or parts, components, or full data of learning process including recorded video lecture at a classroom, synchronized cognitive performance of a user along or during the lecture, synchronized cognitive performance of student along or during the review, rehearsal, contents of notes, comments, questions, searches, and the navigating system for the content of the identified document.

There is also a need in the art to exchange, discuss, and improve the learning process via a network to help the users learn the material in a more efficient way and help the lecturer to improve the teaching process by providing better feedback regarding the lecture so that the lecturer can present the material in an easy, effective, and interesting fashion. There is a need in the art to improve the information intake process and the information presentation process.

SUMMARY

According to exemplary, non-limiting embodiments, cognitive assistant system is provided based on captured synchronized visual and audio information, captured synchronized user's cognitive states information, a display, an intuition-based navigating map and a note or a comment input by a user.

According to exemplary, non-limiting embodiments, intuition-based navigating map is provided based on a script window embodying subtitle modules displayed in sub-windows and marked with user's synchronized cognitive states.

According to exemplary, non-limiting embodiments, captured synchronized visual and audio information is divided into sub-videos or episodes which are synchronized with subtitle modules displayed in sub-windows and marked with user's synchronized cognitive states.

According to exemplary, non-limiting embodiments, the sub-videos which are synchronized with subtitle modules displayed in sub-windows and marked with user's synchronized cognitive states may be added with correlated notes, comments, sketch and so on as input by a user.

Illustrative, non-limiting embodiments may overcome the above-noted disadvantages and problems in the prior art, and also may have been developed to provide solutions to other disadvantages and problems that were not described above. However, a method, an apparatus, a system, and a computer readable medium that operates according to the teachings of the present disclosure is not necessarily required to overcome any of the particular problems or disadvantages described above. It is understood that one or more exemplary embodiment is not required to overcome the disadvantages described above, and may not overcome any of the problems described above.

According to an aspect of exemplary embodiments, a personal emotion-based cognitive assistant system is provided, which includes at least one apparatus configured to capture, from an environment, data including at least one of visual and audio information, at least one sensor configured to capture emotional state of a user corresponding to the data captured by the apparatus, a review apparatus including a memory and a processor. The processor is configured to: divide the data captured by the apparatus into a plurality of segments according to a predetermined criteria, for each of the plurality of segments, determine an intuitive state of the user, comprising a type of correlations and a level of correlations, generated from a comparison between predetermined components of the emotional state of the user captured by the sensor which corresponds to the respective segment, from among the plurality of segments, and distinctive reference signals stored in the memory, wherein the distinctive reference signals represent distinctive intuitive reference samples, generate at least one timeline, and control to display the generated timeline comprising an emotional indicator for each of the plurality of segments. The emotional indicator indicates the determined intuitive state of the user.

According to yet another exemplary embodiment, a personal emotion-based cognitive assistant method is provided. The method includes receiving, by a computer, data including at least one of visual information and audio information captured from environment, receiving, by the computer, an emotional state of a user corresponding to the data captured by at least one sensor, dividing, by the computer, said data into a plurality of segments according to a predetermined criteria, for each of the plurality of segments, determining, by the computer, an intuitive state of the user comprising a type of correlations and a level of correlations, generated from a comparison between predetermined components of the received emotional state of the user which corresponds to the respective segment, from among the plurality of segments, and a plurality of distinctive reference signals stored in the memory. The distinctive reference signals represent distinctive intuitive reference samples. The method further includes generating, by the computer, at least one timeline for the data. The timeline includes an emotional indicator for each of the plurality of segments, which indicates the determined intuitive state of the user, and outputting, by the computer, the generated timeline and at least a portion of the received data.

According to yet another exemplary embodiment, a non-transitory computer readable recording medium storing therein a personal emotion-based cognitive assistant method is provided. When the method is executed by a computer, it causes the computer to: receive data including at least one of visual information and audio information captured from environment, receive an emotional state of a user corresponding to the data captured by at least one sensor, divide said data into a plurality of segments according to a predetermined criteria, for each of the plurality of segments, determine an intuitive state of the user including a type of correlations and a level of correlations, generated from a comparison between predetermined components of the received emotional state of the user which corresponds to the respective segment, from among the plurality of segments, and a plurality of distinctive reference signals stored in the memory. The distinctive reference signals represent distinctive intuitive reference samples. The computer further generates at least one timeline for the data, the at least one timeline includes an emotional indicator for each of the plurality of segments, which indicates the determined intuitive state of the user, and outputs the generated timeline and at least a portion of the received data.

BRIEF DESCRIPTION OF THE DRAWINGS

The accompanying drawings, which are incorporated in and constitute a part of this specification exemplify exemplary embodiments and, together with the description, serve to explain and illustrate exemplary embodiments. Specifically.

DETAILED DESCRIPTION OF EXEMPLARY EMBODIMENTS

Figure 1A:
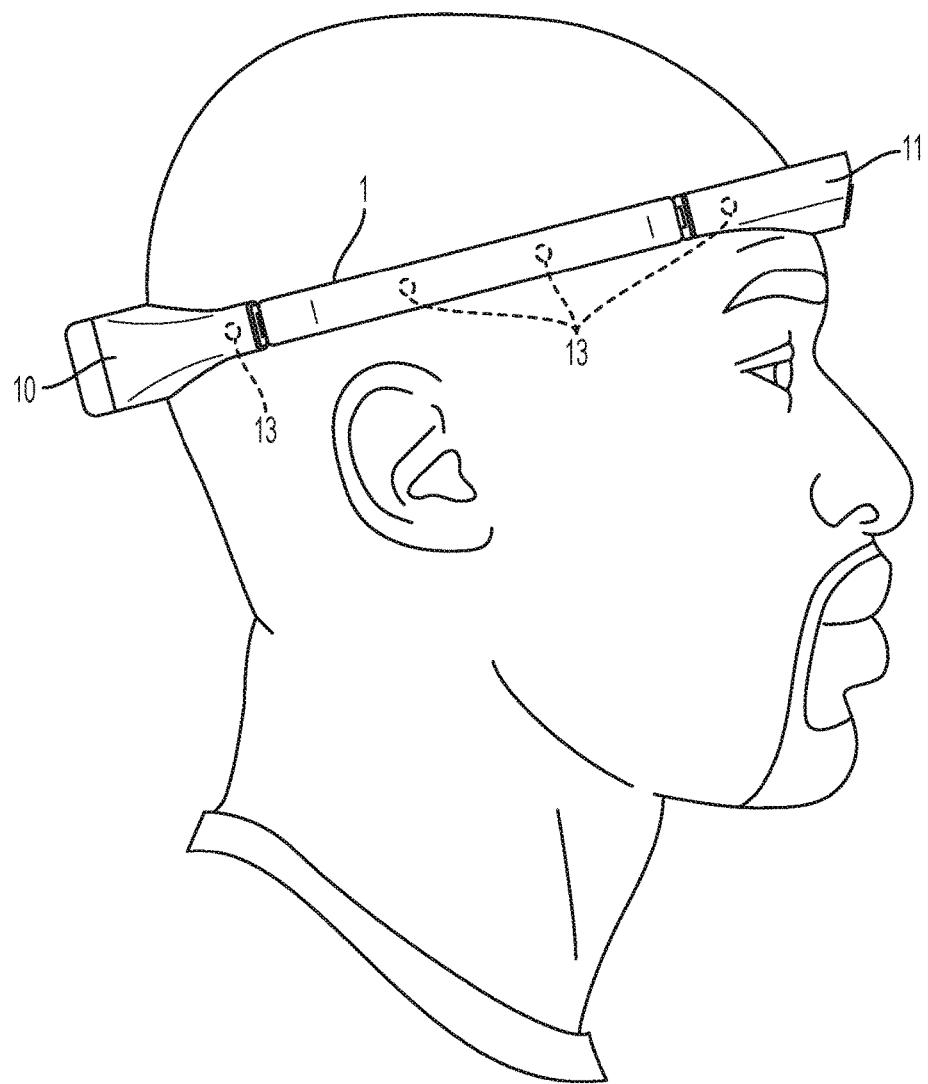
FIG. 1A is a view illustrating a device which captures environment of a user such as video lectures and synchronized cognitive states sensory data, according to an exemplary embodiment.

Exemplary embodiments will now be described in detail with reference to the accompanying drawings. Exemplary embodiments may be embodied in many different forms and should not be construed as being limited to the illustrative exemplary embodiments set forth herein. Rather, the exemplary embodiments are provided so that this disclosure will be thorough and complete, and will fully convey the illustrative concept to those skilled in the art. Also, well-known functions or constructions may be omitted to provide a clear and concise description of exemplary embodiments. The claims and their equivalents should be consulted to ascertain the true scope of an inventive concept.

According to exemplary, non-limiting embodiments, cognitive assistant system is provided based on captured synchronized visual and audio information, captured synchronized user's cognitive states information, a display, an intuition-based navigating map and a note, comment input by a user for example.

According to exemplary, non-limiting embodiments, intuition-based navigating map is provided based on a script window embodying subtitle modules displayed in sub-windows and marked with user's synchronized cognitive states, as explained in greater detailed below.

According to exemplary, non-limiting embodiments, captured synchronized visual and audio information is divided into sub-videos or episodes which are synchronized with subtitle modules displayed in sub-windows and marked with user's synchronized cognitive states.

According to exemplary, non-limiting embodiments, the sub-videos which are synchronized with subtitle modules displayed in sub-windows and marked with user's synchronized cognitive states may be added correlated notes, comments, and/or sketch.

In related art, for example, neuroscience shows that all human mental functions are based on our memory or insights including declarative and non-declarative memory or implicit and explicit memory. See e.g., Eric R. Kandel, "We are what we remember: memory and the biological basis of individuality", Public Lecture Royal Society, https://www.youtube.com/watch?v=skyvzMxtLu8&feature=youtu.be, last visited Dec. 11, 2017, which is incorporated by reference for its helpful background.

The process to build up insights (or process of learning) may include: sensing the meaningful information into working memory, establishing correlations or chunks and making a repetition or rehearsing then distributing and storing this information in different areas of the brain through biological processes. The process of comprehensive learning is the process to build new long-term memory from new short-term memory and the process requires at least one of the three conditions: first, correlation establishment, second, a repetition and/or emotional stimulation see e.g., Frank Longo, "Learning and Memory: How it Works and When it Fails", Stanford University, https://www.youtube.com/watch?v=a_HfSnQqeyY&t=1846s, last visited Dec. 11, 2017 and Eleanor Maguire, "The neuroscience of Memory", The Royal Institution, https://youtu.be/gdzmNqTLakg, last visited Dec. 11, 2017, "Learning How to Learn," Barbara Oakley, https://youtu.be/vd2dtkMINIw, last visited on Jan. 7, 2018, and "How We Learn Versus How We Think We Learn" Robert Bjork. Distinguished Research Professor in the UCLA Department of Psychology, https://youtu.be/oxZzoVp5jmI, last visited on Jan. 10, 2018, which are incorporated by reference for their helpful background.

For example, U.S. Pat. No. 9,711,056 to Nguyen (same inventive entity) describes capturing, detecting and identifying different types of emotional stimulation generated by human's organs while the human is exploring and observing the environment, incorporated by reference for its helpful background.

However, there is a need to build an apparatus, a method, and a system to capture the observation and the emotions, display the captured material, build correlations between the observation and insights, perform repetition and monitoring the emotional stimulations of the learning process to enhance the ability of human learning.

Another example of learning enhancement by capturing the information of the process with synchronized emotional information then reviewing for improvement of the process is provided below.

A golf teacher can set up a camera to capture the swing of golf learners. Then, the teacher can use a software to analyze the motion of golfer's forehead to determine the quality of a swing, a chipping, or a putting.

However, the result of this method has some limits because the motion of the head is small and vary depending on the distance from camera position to the head which the player usually move from shot to shot.

There is a need in the art to improve this process. According to an exemplary embodiment, a camera is placed on the head of a golfer and the camera captures what the golfer observes in which the golf ball is the most important element. Accordingly, the golfer should keep observing and keep the distance from his forehead to the ball stable until the club head impacts the ball.

Also, there is a need to capture synchronized golfer's emotional signals during his or her swing, and then, analysis and the learning process for the golfer can be improved during the review process after the round of the game has been played. In an exemplary embodiment, information gathered by the camera reflects the concentration of a golfer during his swing or putting which very much influences the quality of the swing or the putting.

As described in the U.S. Pat. No. 9,711,056, mentioned above and incorporated herein by reference, human cognitive state may be captured based on emotional and/or sensory data obtained from a user and synchronized with the environmental data. For example, FIG. 1A is a view illustrating a device which captures sensory and emotional data according to an exemplary embodiment.

As shown in FIG. 1A, one or more cameras 11 may be provided on a headset 1 according to an exemplary embodiment. That is, a left camera, a central camera, and a right camera (not shown) may be provided to capture visual data and/or audio data according to an exemplary embodiment. In an exemplary embodiment, one video camera 11, which includes a microphone to capture audio data, may be provided on a front of the headset 1. These are provided by way of examples and not by way of a limitation. One of ordinary skill in the art would readily appreciate that visual data and/or audio data may be captured with a personal device such as a user's personal data assistant or a cellular telephone. Additionally, one of ordinary skill in the art would readily appreciate that any number of cameras and/or microphones may be used and that the visual data and/or audio data may be provided by a single camera or by a plurality of cameras, by a separate microphone or a plurality of microphones. The captured visual and audio data (VI) may then be transferred to an electronic board 10, which includes at least a memory coupled with a processor (not shown).

In an exemplary embodiment, the electronic board 10 may process sensory information and emotional information to generate cognitive state of a user. In yet another exemplary embodiment, the generated cognitive sensory information may be transmitted to another remote device for storage, monitoring or further processing via a communication interface (not shown) provided on the headset 1. For example, the headset 1 may include a communication interface (e.g., a network card, an antenna, and other interfaces known to one of ordinary skill in the art or later developed) to transmit the data wirelessly e.g., a Bluetooth, Infrared, WiFi, and/or a cellular network to a remote server or a cloud for further storage, processing or monitoring and co-supervising. The communication interface may be built into the electronic board 10 or may be provided as a separate device on the headset 1.

In an exemplary embodiment, one or more emotional sensors or cognitive state sensors 13 are further provided on a headset 1. While FIG. 1A depicts four cognitive state sensors, this is provided by way of an example and not by way of a limitation. One of ordinary skill in the art would readily appreciate that a single sensory or cognitive state sensor may be used but preferably multiple cognitive state sensors are provided to capture cognitive state of a user. The cognitive state sensors 13 may be provided on both sides of the headset 1. In an exemplary embodiment depicted in FIG. 1A, only one side of the user's head is shown but the other side may also include four cognitive state sensors 13 that detect the cognitive state of the user. That is, in an exemplary embodiment, cognitive state is obtained from multiple sensors 13 by detecting activities in various parts of the brain.

According to an exemplary embodiment, raw EEG signals obtained from the cognitive state sensors are combined and synchronized with the video and audio signals. In an exemplary embodiment, the raw EEG signals embody cognitive distinctive instinct components. In an exemplary embodiment, EEG signals are filtered at distinctive reference signals to detect ET 10 component for evident states towards explorative/learning observations, ET 9 for confident states towards evident observations to obtain attentive cognitive state of the user, as explained in greater detail below. The output of the filter is at different levels based on different attentive state of the user. That is, the EEG frequency and amplitude change based on user's emotional level or cognitive state. In an exemplary embodiment, inactivity means that the amplitude of all of the EEG components at a identified frequency are below a predetermined threshold value. Accordingly, in an exemplary embodiment, a determination can be made that a user is sleeping or not paying attention. According to an exemplary embodiment, a plurality of cognitive state sensors 13 generate respective channel signals (ET9-ET10 for example), as explained in greater detail below with reference to FIG. 1B. The respective channel signals are used to determine the cognitive state of a user wearing the headset 1.

EEG is provided by way of an example and not by way of a limitation. According to an exemplary embodiment, when the discrimination between certain EEG components and referenced signals are above a predetermined threshold value or above predetermined respective threshold values that means that the user is at an identified state such as evident (correlated, known), confident (well-correlated, experienced) and so on. For some examples, see U.S. Pat. No. 9,711,056, which is incorporated by reference.

According to an exemplary embodiment, the cognitive state sensors 13 may be positioned around the frontal lobe of the user to detect executive emotions of the user such as the user being desired, concerned, evident or confident. For example, as shown in FIG. 1 B, five cognitive state sensors 13 (S1-S5) are placed around the frontal lobe of the user and output respective sensory signals ss1-ss5. In an exemplary embodiment, if the ET 10 signals detected from sensors 51 and S3 output respective signals above predetermined respective threshold values, a determination can be made that the user feel evident, e.g., the observation is known. If the detected ET 11 signals from sensors S2, S4, and S5 output respective signals above predetermined respective threshold values, a determination can be made that the user feel comfortable and/or expected a good result.

In an exemplary embodiment, because the user reads text from top to bottom (i.e., from the upper line to the lower line), therefore signals of voice which are interpreted synchronously with the text lines. As such, in an exemplary embodiment depicted in FIG. 1B, audio signals i.e., voice output, is displayed in a vertical line(s) and the timeline is also displayed in a vertical direction, for consistency with the text.

Figure 1B:
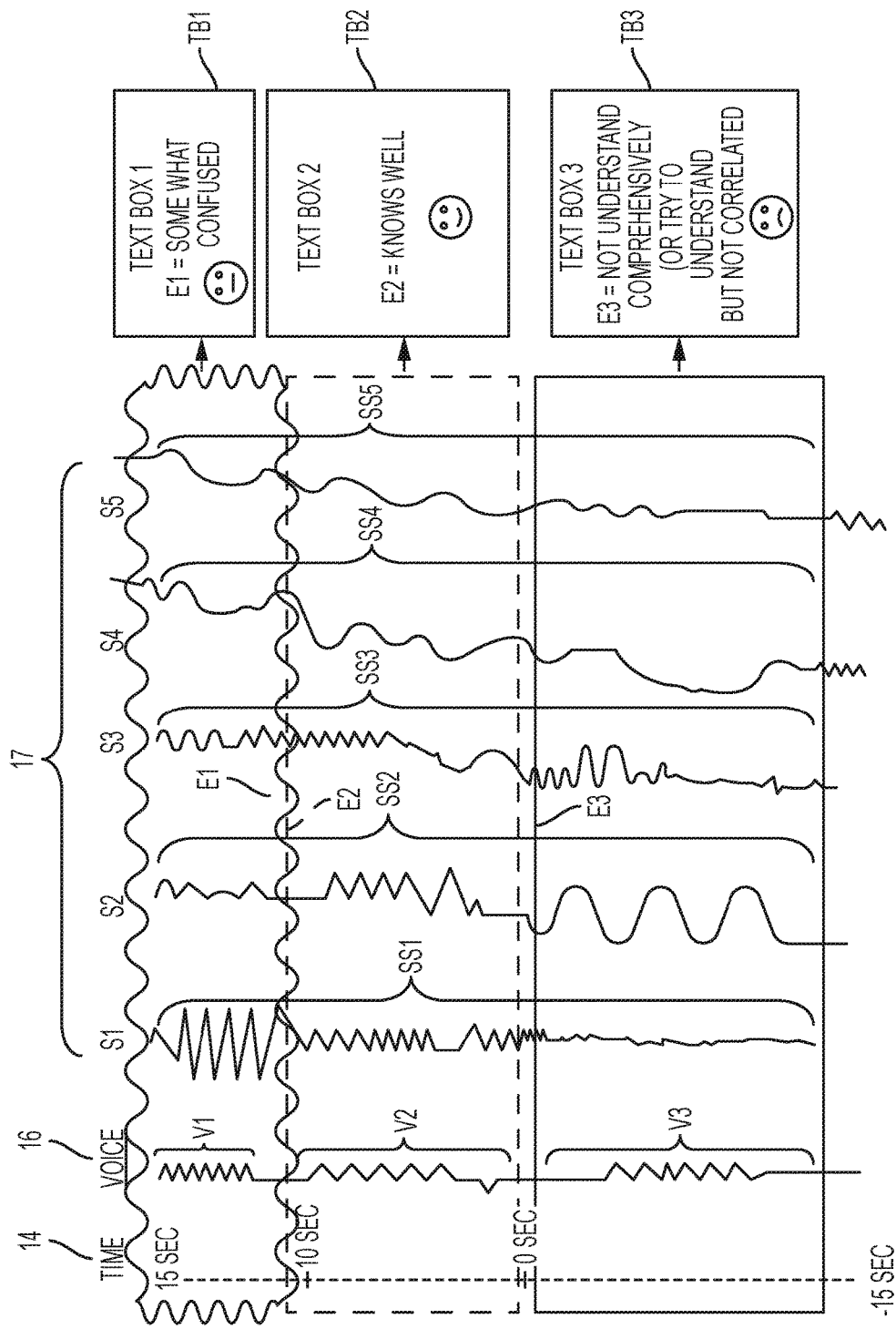
FIG. 1B is a view illustrating synchronized cognitive states sensory data captured by the sensors and interpreted to correspond to a classified cognitive state of a user, according to an exemplary embodiment.

FIG. 1B, according to an exemplary embodiment, depicts voice signals captured for a duration of 30 seconds. For example, a timeline 14 is depicted on the left side of FIGS. 1B and 1s split into intervals depicted by 15 seconds point, 10 seconds point, 0 seconds point and −15 seconds point. The 15 seconds mark depicts voice data already played and the −15 seconds mark depicts voice data to be played in 15 seconds. 0 seconds mark indicate the current position of the voice data being output. FIG. 1B further shows voice signals 16 that has 2 durations at low level, from −2 s to +1 s and from +9 s to +11 s, which would indicate a period of silence or a pause between the spoken words. In an exemplary embodiment, these durations separate the continuous voice signals into modules which embody independent meanings. According to an exemplary embodiment shown in FIG. 1B, voice data 16 is separated into three separate voice modules, V1, V2, and V3. In an exemplary embodiment, the voice data 16 is split into three voice modules V1, V2, and V3 based on natural breaking points in a recorded voice such as when a pause is made or when a sentence is finished, which can be detected based on recorded voice intonation, which will correspond with an amplitude.

According to an exemplary embodiment, based on the split voice modules or segments V1, V2, V3, voice to text conversion is performed. That is, voice data is converted into text data and may be displayed to the user. In an exemplary embodiment, one text box is provided for each voice segment or module. For example, as depicted in FIG. 1B, the text, obtained from converting the voice signal, is displayed in respective text boxes TB1-TB3. That is, the first text corresponding to the converted voice segment V1, is displayed in the text box TB1; the second text corresponding to the converted voice segment V2, is displayed in the text box TB2; and the third text corresponding to the converted voice segment V3, is displayed in the text box TB3. In an exemplary embodiment, text output corresponding to the converted voice is placed into three corresponding windows, which are TB1, TB2, and TB3 depicted in FIG. 1B. In an exemplary embodiment, the number of sub-windows being displayed will correspond to the number of voice segments generated during the division of continuous voice output. As shown in FIG. 1B, cognitive state of the user is also displayed as five cognitive state signals (ss1-ss5) 17 obtained from the sensors S1, S2 . . . S5. These cognitive state signals are also displayed synchronized with voice signal in the vertical direction. According to an exemplary embodiment, the cognitive state signals ss1-ss5 are also split into segments corresponding to the voice segments V1-V3. That is, in an exemplary embodiment, the cognitive state signals are analyzed in segments which correspond to the voice segments to determine an emotional state of the user.

As shown in FIG. 1B, E1 is a cognitive state obtained from analyzing signals ss1, ss2, ss3, ss4, and ss5 produced at time 15 sec to 10 sec and corresponding to the voice segment V1, the text of which is displayed in the TB1 box. In an exemplary embodiment, E1 is interpreted to correspond to an emotional state 1 and can be marked with a first color (e.g., blue) to indicate that the user is somewhat sleepy or unsure of at least some of the material corresponding to the voice segment V1. That is E1 indicates a state in which the user appears to be somewhat confused (not entirely confident) with the material in the voice segment V1. E2 is the cognitive state obtained from signals ss1-ss5 recorded during the time the user hears voice V2 with content displayed in TB2. E2 is interpreted to correspond to an emotional state 2 and can be marked with a second color (e.g., green) to indicate that the user knows and/or understands the material (voice segment V2). E3 is the emotional state obtained from signals ss1-ss5 recorded during the time the user hears voice V3 with content displayed in TB3. E3 is interpreted to correspond to an emotional state 3 and can be marked with a third color (e.g., red) to indicate that the user try to focus but does not yet understand the material (voice segment V3). The marking depicted in FIG. 1B are provided by way of an example only and not by way of a limitation. According to another exemplary embodiment, the text in the respective text boxes TB1-TB3 can be color coded based on the determined emotional state (E1-E3) of the user. As an alternative, various marking and indicators could be used to depict the user's state including % signs, color shading within various colors used and so on. According to an exemplary embodiment, the voice signal 16 may be a voice of a presenter giving a lecture in a classroom for example. Contents depicted on a blackboard or projected onto screen maybe recorded as visual data and stored in synchronization with the audio signals output by the presenter, for example.

Figure 1C:
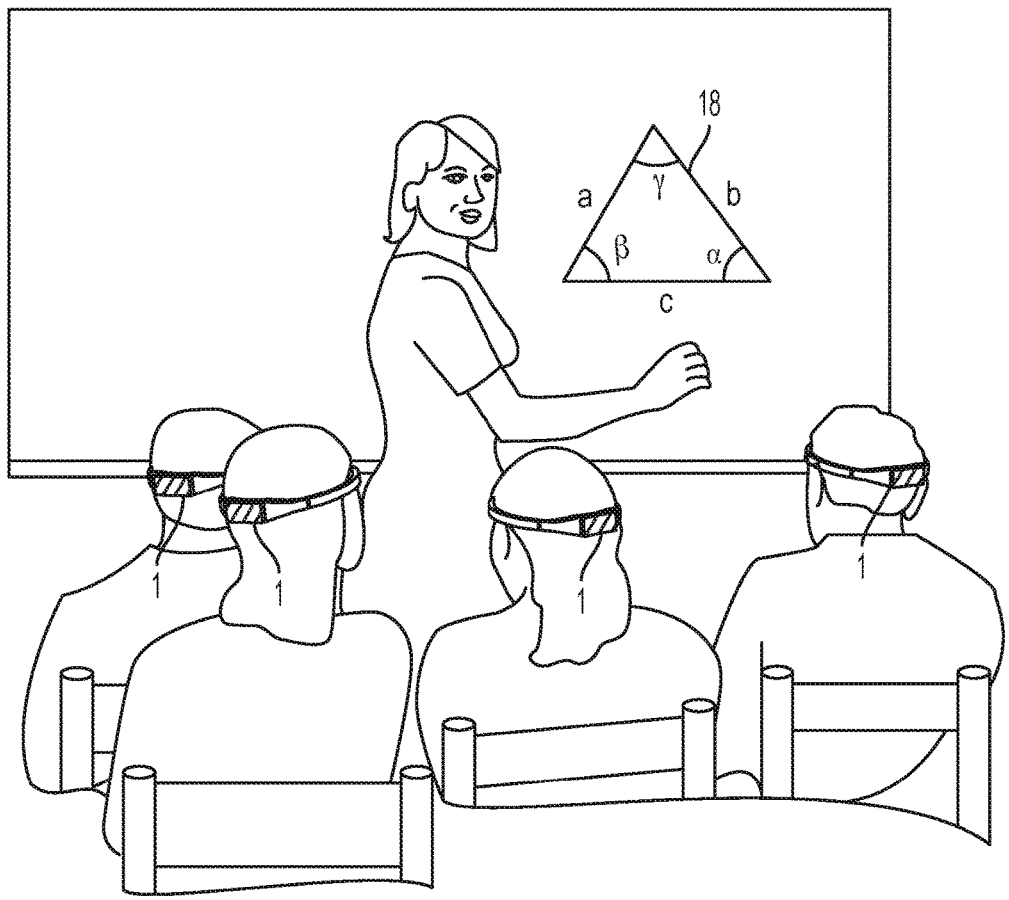
FIG. 1C is a view illustrating the devices in a practical use for capturing video lecture and synchronized cognitive states sensory data in a classroom, according to an exemplary embodiment.

As shown in FIG. 1C, the presenter may be giving a lecture presenting certain content or information to a user. The presenter may show an example 18 of the content being presented, on a blackboard. A plurality of students may be wearing headsets 1 and observing the lecture. Each one of the headset 1 worn by each or some of the plurality of students may output respective cognitive state of the respective user for each portion of voice signal of the presenter. The plurality of cognitive states of the plurality of users/students may be combined to provide output to the presenter such as this portion of the lecture is confusing, this portion is boring, or this portion is well understood. Using this feedback, the lecturer may improve his or her presentation material by simplifying concepts that confuse the students and/or shortening presentation of the contents that is understood well. These are provided by way of an example only and not by way of a limitation.

Figure 1D:
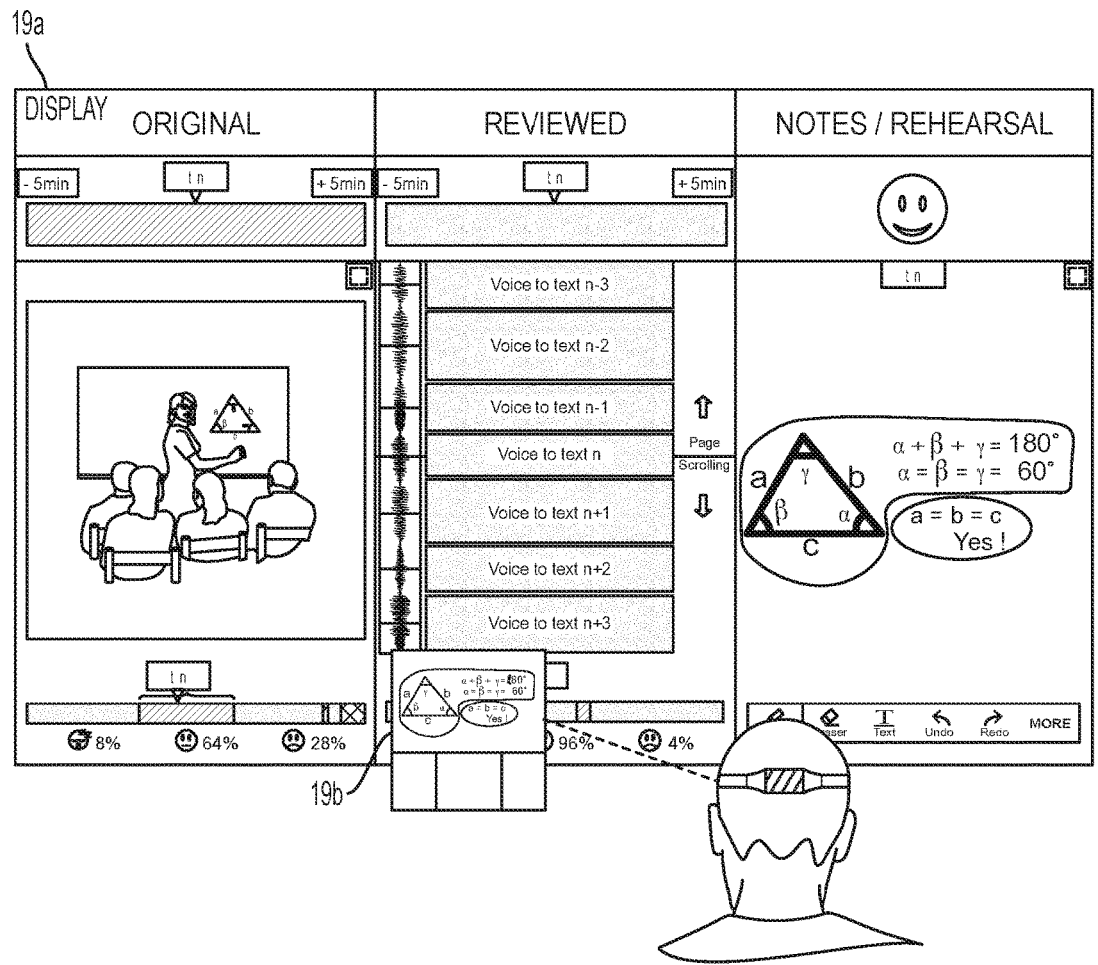
FIG. 1D is a view illustrating reviewing, rehearsing, and consolidating of a recorded content such as a lecture based on synchronized classified cognitive states of a user, according to an exemplary embodiment.

FIG. 1D is a view illustrating reviewing, rehearsing, and consolidating of a recorded content such as a lecture based on synchronized classified cognitive states of a user, according to an exemplary embodiment. According to an exemplary embodiment depicted in FIG. 1D, a user or a student is reviewing and/or studying the lecture using a large display 19a such as a television and a separate remote controller such as a touch screen or a sketch pad 19b. The touch screen 19b may include an iPad, a mobile terminal, a universal remote controller, and so on. These are provided by way of an example and not by way of a limitation. According to an exemplary embodiment, the touch screen 19b is mainly for input of notes and/or sketches, for controlling and/or navigating the display device 19a, and is not primarily intended for displaying images and/or video. According to an exemplary embodiment, it is especially convenient when working in groups and/or working at home where a big screen is available.

As shown in FIG. 1D, the display 19a outputs a playback of video data captured during the lecture in a left portion of the screen, the converted corresponding voice data may be displayed as text segments in the middle of the screen, as well as output via a speaker in its audio form, and user notes captured during the initial lecture and/or made during review may be depicted on a right side of the screen on the right portion of the screen, which will be explained in greater detail below with reference to FIGS. 8A-9C.

Figure 2:
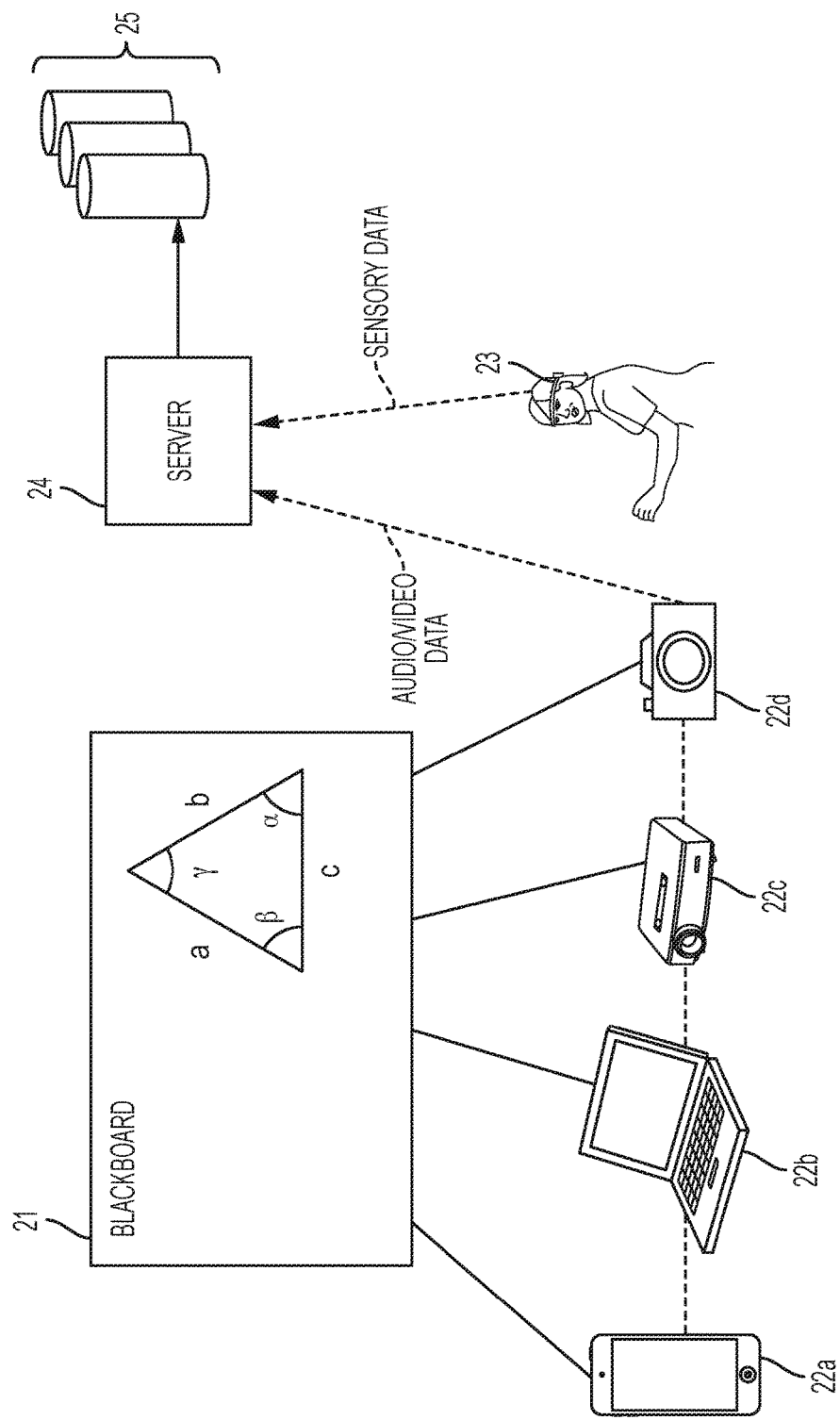
FIG. 2 is a block diagram illustrating a system capturing lecture material and sensory data, according to yet another exemplary embodiment.

FIG. 2 is a block diagram illustrating a system capturing lecture material and sensory data according to yet another exemplary embodiment. In FIG. 2, the user records a lecture e.g., topics and/or notes provided by the lecturer on a blackboard 21, for example. Additionally, the user may also record audio data such as explanations provided by the lecturer along with the illustrations depicted on the blackboard 21. The user may record via one or more of a plurality of personal devices 22a . . . 22n such as a smart phone 22a, a personal computer or a notebook 22b, a video recorder 22c, and a camera 22n. These devices are provided by way of an example only and not by way of a limitation.

In an exemplary embodiment, the audio and video data may be output directly to a server 24. The audio and video data is output to a server 24 with a corresponding time stamp(s) e.g., every 10 seconds of recording is transmitted to a server 24 via a network such as Internet, WiFi, Bluetooth, and so on. Although the server 24 is depicted in FIG. 2 as a separate device, the server 24 may be located in a personal computer 22b or some other personal device 22a . . . 22n depending on the processing power and memory of the personal device.

The user may be wearing a headset 23, which monitors the user's cognitive state. The headset 23 is provided by way of an example only and not by way of a limitation. In an exemplary embodiment, the user may be wearing another device that would include a number of sensors to measure the cognitive state of the user via sensors described with reference to FIG. 1A. In an exemplary embodiment, signals detected by the sensors are used to determine the cognitive state or the emotional state of the user.

In an exemplary embodiment, as explained above with reference to FIG. 1B, a human brain outputs low explorative signals while the user is relaxing and not concentrating (ET9-ET10-ET11-ET12). Low explorative signals indicate that the user is not actively learning. On the other hand, in an exemplary embodiment, amplitude at identified frequencies of explorative signals change as the user is interested and paying attention (ET1-ET12). According to an exemplary embodiment, different amplitude bands (at different identified frequency bands) provide for detecting different cognitive or emotional state of the user i.e., determine variations in the cognitive or emotional state of the user.

In an exemplary embodiment, 8 channel EEG signals may be captured from the user and based on these captured signals, it may be determined whether the user is paying attention and the level of understanding the material being presented For example, whether the user is sleepy, wandering, not paying attention to the topic (may have a strong sense of being bored or tired). 8 channel EEG signals are provided by way of an example only and not by way of a limitation.

In an exemplary, the sensory data may be saved in a memory card within the headset 23. In another exemplary embodiment, the sensory data may be periodically output via a network to the server 24. By way of an example, the network may include Internet, WiFi, Bluetooth or even a wired network e.g., the headset is connected via a wire to the server 24, which may be located in the personal device 22a . . . 22n. In an exemplary embodiment, the sensory data e.g., accumulated 10 seconds interval, by way of an example, is output to the server 24 with a time stamp for further processing.

The server 24 includes a processor and a memory, as detailed below with reference to FIG. 3. In an exemplary embodiment, the server 24 may compare time stamps of the audio/video data (hereinafter referred to as contents or environmental data) and the sensory data to generate cognitive or emotional status of the user, which may then be stored in a memory 25. The memory 25 may include one or more databases, internal or remote to the server 24.

Figure 3:
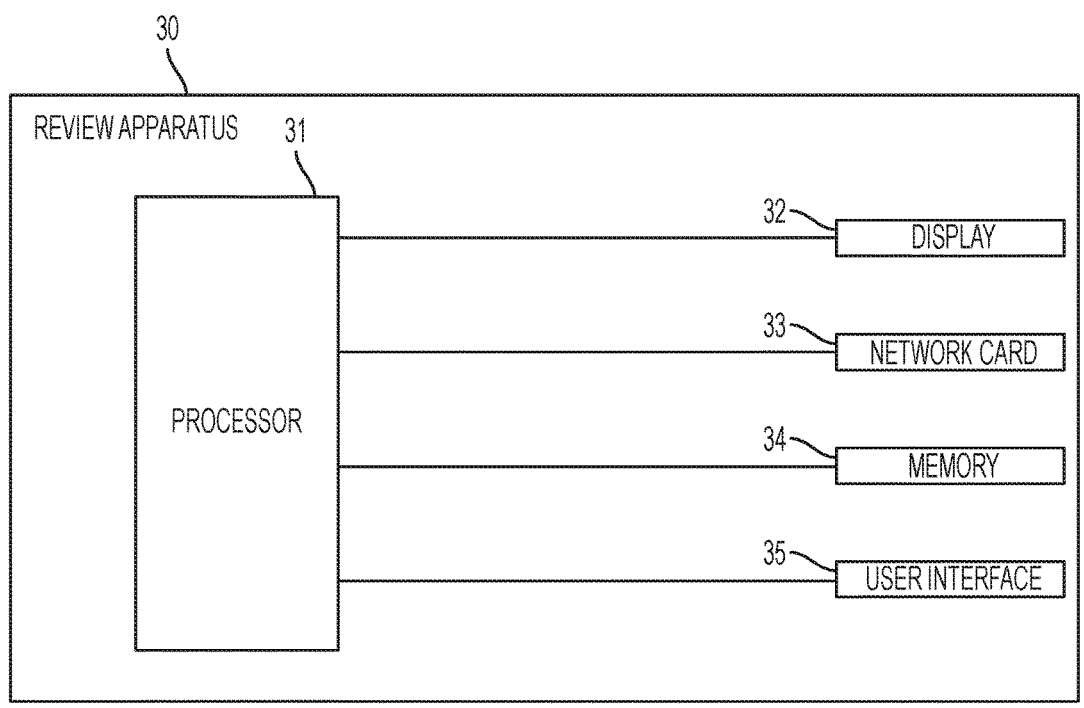
FIG. 3 is a block diagram illustrating a review apparatus, according to an exemplary embodiment.

In an exemplary embodiment, as shown in FIG. 3, a server 30, is a review and/or processing apparatus, which includes a processor 31, which may be a central processing unit (CPU), which controls the apparatus and its hardware components and executes software instructions stored in one or more memories such as a memory 34. By way of an example, the processor 31 may also include a random access memory (RAM), a read only memory (ROM), one or more graphical processes, interfaces, and so on. Components of the processor 31 may be connected to each other via a bus. The processor 31 is further connected to and controls a display 32, which outputs recorded or original video signals in various forms and formats. The display 32 includes a speaker which outputs an audio sound. This is provided by way of an example and not by way of a limitation. Multiple speakers may be provided and maybe external to the display 32. The processor 31 may be connected to a network interface or a network card 33, which may include a WiFi chip, a Bluetooth chip, wireless network chip, and so on. The network card 33 may further include one or more ports for wired connections. Additionally, the apparatus 30 may include a memory 34, which may store one or more of executable instructions which when executed by the processor 31 cause the processor to control the apparatus 30 and its components. The memory 34 may further store audio and video data (contents) generated by one of the devices 22a to 22n (see e.g. FIG. 2). The apparatus 30 may further include a user interface 35, which may include buttons, keyboard, a mouse, a USB port, a microphone, a gesture sensor, and so on. The user interface 35 receives user input in various formats such as gestures, audio via a microphone, keyboard, mouse, touch screen, and so on, provided by way of an example and not by way of a limitation.

Figure 4:
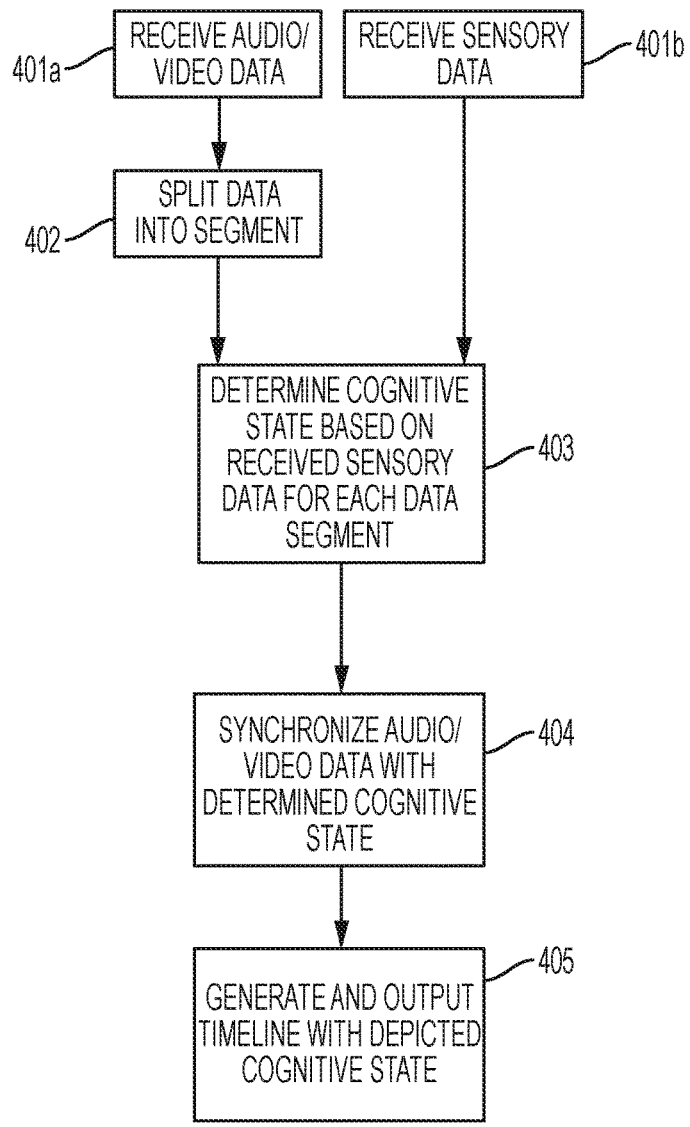
FIG. 4 is a flowchart illustrating a method of generating a timeline, according to an exemplary embodiment.

In an exemplary embodiment, the processor 31 compares time stamps of the audio/video data with time stamps of the sensory data and generates a timeline for the contents. FIG. 4 is a flowchart illustrating a method of generating a timeline according to an exemplary embodiment. In an exemplary embodiment, visual, audio, and cognitive data may be synchronized by a clock of the system (controlled by CPU). The system captures synchronized visual, audio, and cognitive information in real-time then stores the synchronized raw material in a memory card, by way of an example. When reviewing, a software application filters from the raw cognitive information at different reference frequencies to detect cognitive states at different durations in real-time. Based on the synchronization, the system can infer different cognitive states of user along the lecture in real-time using the software application embodied on a non-transitory computer-readable medium and executed by a processor.

Also, in an exemplary embodiment, during the reviewing, the video and analyzed user's cognitive statuses maybe prepared in advance and not in real time.

As shown in FIG. 4, in operation 401a, the apparatus receives environmental data such as audio and/or video data and in operation 401b, the apparatus receives the sensory data from the sensors, for example, worn by the user. These are provided by way of an example only and not by way of a limitation. According to yet another exemplary embodiment, the video and/or audio contents may be provided together with the sensory data in a predetermined time intervals such as 10 second intervals. For example, a set of (V, A, E) may be synchronized by sampling frequency where V is visual data, A is for audio data, and E is for emotional state of the user.

In operation 402, the received contents (video/audio data) is split into segments based on continuity of the voice signal. For example, the processor determines where a pause is made or an end of a sentence based on voice intonation. According to an exemplary embodiment, maximum length for a segment may also be set e.g., 5 seconds. In an event, a pause or an end of sentence is not found in voice data of one minute duration, the voice is segmented at five seconds point (five seconds interval blocks). This is provided by way of an example only and not by way of a limitation. In an exemplary embodiment, "evident" and "confident" frequency is used to detect explorative cognitive states of a user. These two main signals reflects user's correlations of recent observation and insights. For example, known or unknown or evident or strange states are being used. In an exemplary embodiment, emotional signals which relate to survival and reproductive area (e.g., ET 1 to ET 8) like, love, scared, closed, open are not being used.

In operation 403, the cognitive state of the user is determined (ET9-ET10) based on the processed sensory data for each segmented portion of the data i.e., for each piece of contents. As explained above, when the sensors on a certain part(s) of the brain output signals of a first amplitude (small amplitude) in one or more frequency bands, the apparatus may determine that the user is confused and/or scared and/or concerned. On the other hand, when the sensors on another part of the brain output signals with a second amplitude (large amplitude), the apparatus may determine that the user is confident. According to an exemplary embodiment, signals with high amplitude in a first frequency band and low amplitude in a second frequency band may indicate a confused cognitive state of the user, whereas signal with low amplitude in the first frequency band and high amplitude in the second frequency band may indicate confident state of the user. If all of the sensors produce signals of the first amplitude, this may indicate that the user is asleep or not paying attention. This is provided by way of an example only and not by way of a limitation.

For example, according to another exemplary embodiment, the sensory data is used to determine that the user is distracted (ET-1). For example, the headset 1 may detect that the user is looking at the blackboard but his mind is wandering away from the presentation topic or is elsewhere (sleeping). Camera still is recording the lecture. In addition, the apparatus can mark this duration (this time segment) to help the user easily recognize the portion of the lecture to review i.e., what the user has missed in classroom. According to yet another exemplary embodiment, if the sensory data trigger other emotions such as people, food, and/or things outside of the audio/video data, the cognitive state of the user may be determined to be distracted with outside thoughts and not paying attention to the lecture.

In operation 404, the audio/video data (contents) is synchronized or linked with a corresponding determined cognitive state and (optionally) the segmented audio data may be converted into text for a display. In operation 405, a timeline to be displayed is generated, which depicts the cognitive or emotional state of the user, optionally along with a corresponding portion of the audio/video data or contents. In an exemplary embodiment, the timeline may be generated for playing back the audio/video contents obtained during the lecture. The timeline may be color coded based on the determined cognitive or emotional state of the user. That is, a portion of the timeline may be displayed in green for the user knowing the material well, whereas another portion of the timeline may be displayed in red for the contents of the lecture the user is confused about or has not paid attention to. This is explained in greater detail below by way of an example.

Figure 5:
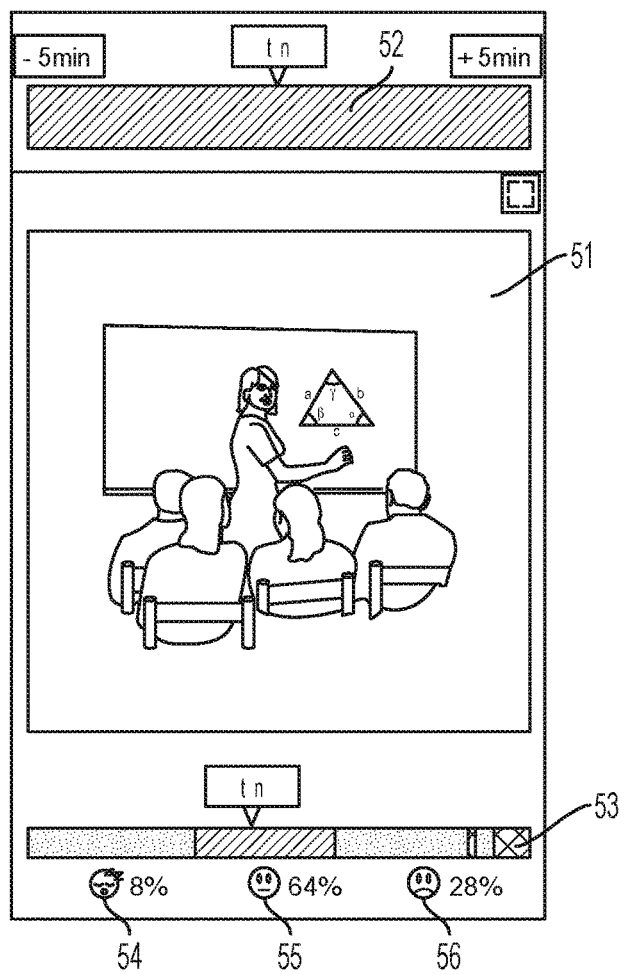
FIG. 5 is a view illustrating displaying contents with cognitive state of a user, according to an exemplary embodiment.

FIG. 5 is a view illustrating contents displayed with corresponding cognitive states of a user according to an exemplary embodiment.

As shown in FIG. 5, the contents 51 is displayed to the user via a display together with a timeline 52, which is known in the art to show the time point of the contents currently being displayed. The contents 51 may include video and audio contents. Additionally, a timeline 53 may be provided and displayed to a user via a display. The timeline 53 depicts the cognitive or emotional state of the user in correspondence with the audio and/or video content. By way of an example, the timeline 53 depicts the cognitive state of the user synchronized with the displayed contents. The cognitive state of the user is selected from among a disinterested state 54 in which the user is not interested or asleep, a confident state 55 in which the user is comfortable with the output contents, and a confused state 56 in which the user does not understand the material provided. These are provided by way of an example only and not by way of a limitation. According to another exemplary embodiment, color coding for various cognitive states may be used and the degree of confidence or confusion may correspond to a particular shade of the color. For example, a dark red color on a timeline 53 may indicate that the user is very confused, a pink color may indicate that the user is just a little confused.

According to another exemplary embodiment, timelines 52 and 53 may be combined into a single integrated timeline which illustrates a point in time currently being displayed with respect to the contents and the cognitive state of the user.

According to various exemplary embodiments, the user may determine portions of the lecture (contents) that are confusing or were missed and practice his or her review session on these portions of the contents. According to various exemplary embodiments, instead of reviewing the entire lecture (contents), the user may focus on the confusing portions or the portions that were missed. Further, cognitive states of multiple users that attend the lecture can provide feedback for the lecturer. For example, if 70% of the users are confused at certain portions of the lecture, the lecturer can determine to revise or simplify materials. On the other hand, if the users (students) are not interested in yet another part of the lecture, the lecturer can revise the lecture to capture user's attention.

According to another exemplary embodiment, a review apparatus is configured to facilitate the study of the material after the lecture was presented.

Figure 6:
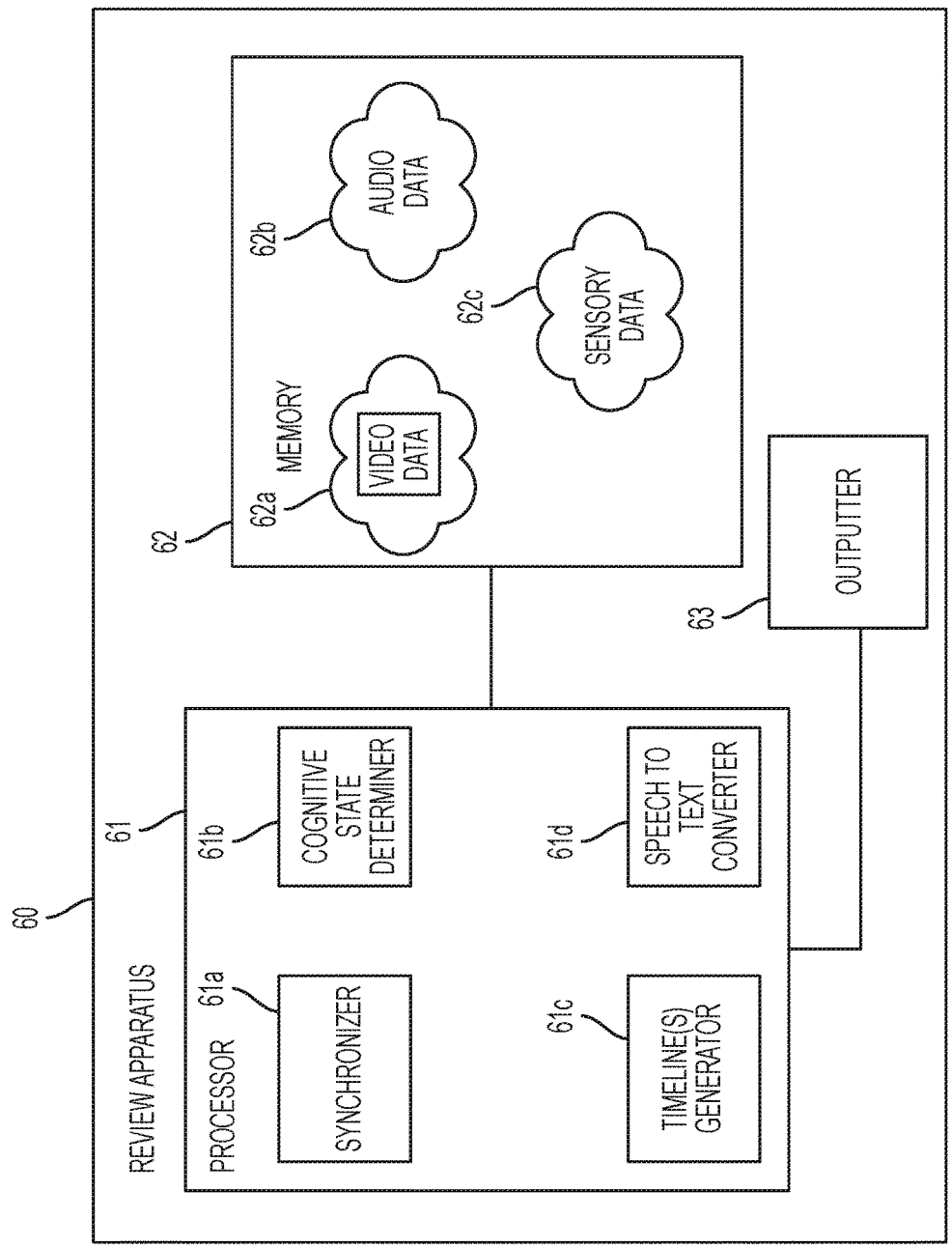
FIG. 6 is a block diagram of a review apparatus, according to an exemplary embodiment.

FIG. 6 is a block diagram of a review apparatus according to an exemplary embodiment.

As shown in FIG. 6, a review apparatus 60 includes a processor 61, a memory 62, and an outputter 63. The memory 62 stores captured video data 62a, captured audio data 62b, captured sensory data 62c, which is captured 8-channels EEG signals. The processor 61 executes a synchronizer 61a, which is configured to synchronize the captured video data 62a, with the captured audio data 62b and the captured sensory data 62c, as described below with reference to FIG. 7, by way of an example. The processor 61 further executes a cognitive state determiner 61b, which determines the cognitive state of the user ET0-ET10, a timeline(s) generator 61c, which generates one or more timelines for audio and video contents and the sensory data using the output from the synchronizer 61a and the cognitive state determiner 61b, and a speech to text converter 61d, described in greater detail below. The environmental audio/video contents, along with cognitive states may be output to a user via an outputter 63 which includes at least one display and speakers.

Figure 7:
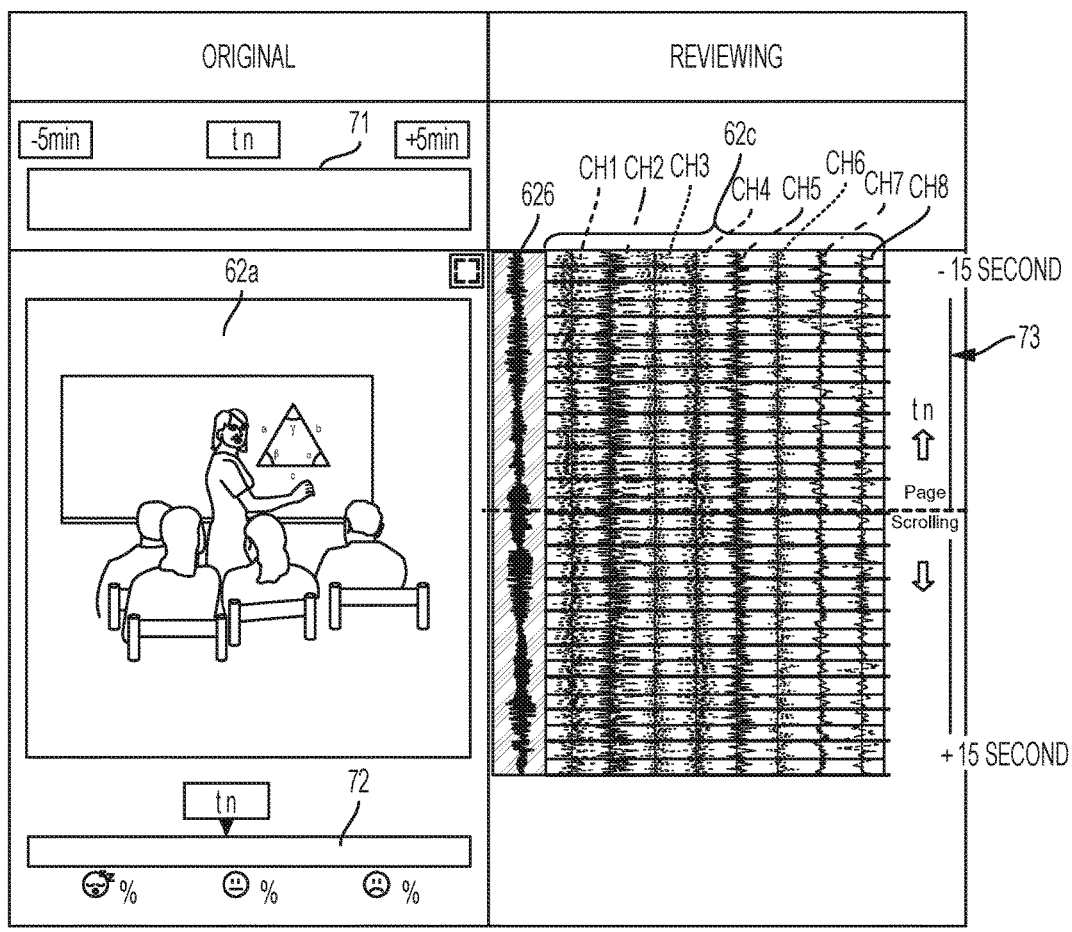
FIG. 7 is a view illustrating synchronization of video and audio contents with sensory data by a review apparatus, according to an exemplary embodiment.

FIG. 7 is a view illustrating synchronization of video and audio contents with sensory data by a review apparatus, according to an exemplary embodiment. FIG. 7 depicts synchronization of raw input data. As shown in FIG. 7, the video data 62a may be displayed on a display along timelines 71 and 72. The timeline 71 may be a timeline for a predetermined interval of the lecture. According to an exemplary embodiment, the timeline 71 is presented for the current time point $t_n$ and five minutes before and after the current time point. The timeline 72 is a timeline for an entire duration of contents. According to an exemplary embodiment, timelines 71 and 72 show progression of the lecture currently being viewed or played, as is known in the art. According to a depicted exemplary embodiment, the video data 62a is displayed at a time point tn and the timelines 71 and 72 show an indicator at a current time point tn. Timeline 71 has a bar for a ten minute interval that is scrollable by a user with points +5 minutes and −5 minutes from the currently displayed time point tn. The timeline 72 has the same time point tn with respect to entire contents of the lecture. In correlation with the video data 62a, audio data 62b is provided. The audio data 62b currently output at the same time point tn and is provided for a 30 seconds interval corresponding to the 30 seconds interval of the video data 62a. Additionally, a time line 73 shows an indicator at a current time point tn. Further, sensory data 62c is synchronized with the audio data 62b and video data 62a. According to an exemplary embodiment, originally captured 8-channel EEG signals, CH1-CH8 are synchronized by the synchronizer 61a. The synchronized cognitive state of the user 62c and synchronized audio 62b may be depicted on the same timeline 73 (−15 second −+15 second). The cognitive state of the user is output in correlation with the video data 62a, audio data 62b. The cognitive state determined from the sensory data 62c, may be indicated on one or more timelines in a form of indicators, shading, coloring, and so on. According to another exemplary embodiment, a dedicated timeline exclusively for the cognitive state of the user may be generated.

According to an exemplary embodiment, the timeline 73 is for the nearest time around $t_n$: 30 seconds. The audio information in this 30 seconds period is displayed in text to enhance the ability of detailed recognition around the $t_n$. The timeline 71 is for the medium-portion of time around $t_n$: 10 minutes. The audio information in this 10 minutes period is displayed along with the cognitive state of the user to enhance the ability of wider recognition and navigation. The timeline 72 is for the full story video: The history of cognitive states along the original video is displayed to enhance the ability of performance evaluation and navigation.

According to an exemplary embodiment, cognitive state signals 62c of the user embodies cognitive distinctive instinct components that are described and claimed in U.S. Pat. No. 9,711,056 for example, ET 10 component for evident states towards explorative/learning observations, ET 9 for confident states towards evident observations, ET 4 for cognitive states towards observations to things, ET 3 for cognitive state towards observations to food. Based on reference cognitive signals, the system can filter and detect the states of the user towards the cognition on the observation of the user e.g., video 62a and/or audio 62b. By a way of example, by filtering the data 62c by ET 10 reference sample, the system can identify the states of user throughout the lecture and grade them at a three levels system, by way of an example. For example, a level 1 indicates that the user is not focused (bored, sleepy, his mind is wandering elsewhere), a level 2 indicates that the user is confident and his knowledge is evident (correlated, known, understood), a level 3 indicates that the user is focused but is confused about the material (no correlations to insights yet). This is provided by way of an example only and not by way of a limitation.

Figure 8A:
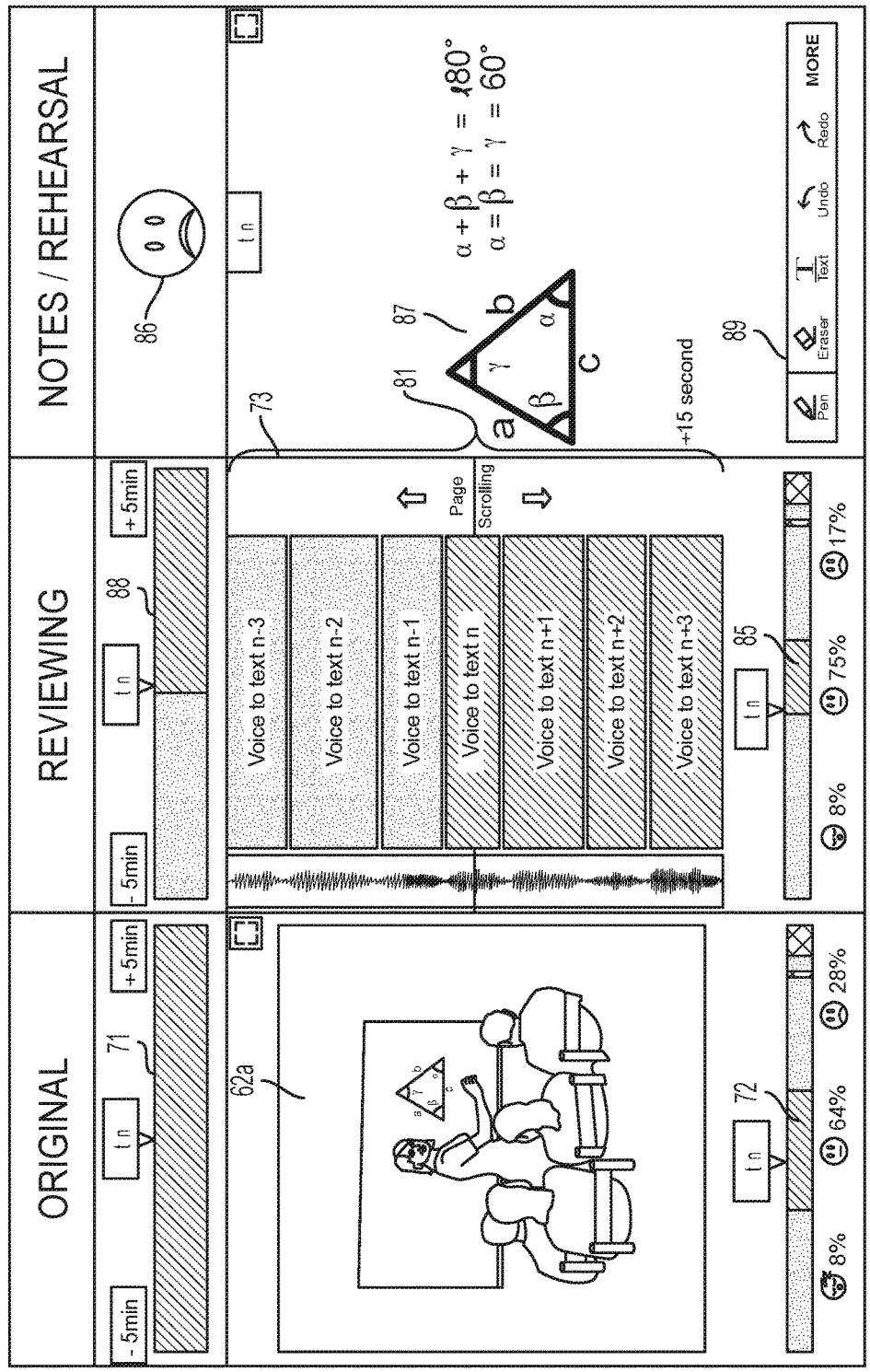
FIGS. 8A and 8B are views illustrating methods of building correlations, according to exemplary embodiments.

FIG. 8A is a view illustrating a method of building correlations, according to an exemplary embodiment.

As shown in FIG. 8A, the user is in a process of reviewing or studying the contents of the original lecture. According to an exemplary embodiment, the speech to text converter 61d splits audio data 81 such as the lecturer's voice into portions, as explained in greater detail above. According to yet another exemplary embodiment, the audio data 81 is split into 5, 10, or 15 seconds intervals (portions before and after the current point (n): n−3, n−2, n−1, n, . . . , n+3, where n is the current portion of the audio data being output such that 30 seconds of content nearest to the current time or current point (n) in a lecture is split) by a speech to text converter 61d. In an exemplary embodiment, the audio contents are separated at intervals between two sentences (or between two meanings, two semantics and so on). Based on this audio signal, the video is also split into discrete videos in meanings and the speech to text converter 61d interprets the voice to convert the audio data to text in portions n−3, . . . , n+3. The displayed video image 62a corresponds to the displayed text portion n and is the currently output video and audio data. Additionally, the text for the audio contents before and after the currently displayed content is also provided as n−3, n−2, n−1 and n+1, n+2, and n+3 segments or modules. According to an exemplary embodiment, each portion is five seconds and the text 81 being displayed corresponds to the timeline 73. In FIG. 8A, visible correlations 15 seconds before and after the recent meanings as shown by the timeline 73. For example, the content of a 30-second video is provided to view in ONE SIGHT. A 30-second video content is visible and is scrollable to be synchronized with video content. The scrolling may appear automatically according to an exemplary embodiment. According to an exemplary embodiment, a user may view full content of 30 second long video at one moment so as to build the correlations between previous 15 seconds content, recent content, and next (future) 15 second content. In related art, a viewer only views a single image in a video at a time. In an exemplary embodiment, however, a viewer may view, at the same time, notes on the right 87, previous 15 seconds of content depicted in an upper portion of audio data 81, and next 15 seconds of content, depicted in a lower portion of the audio data 81, and may also view the video 62a.

In FIG. 8A, timelines 71 and 88 are provided for a 10 minutes interval (medium portion) of the cognitive state history around the currently played content. According to an exemplary embodiment in FIG. 8A, the timelines 71 and 88 are ten minute timelines around the recent content (original) and the recent content (being reviewed), respectively. Accordingly, a view is provided with wider perspectives and correlations from recent content. Similarly, according to an exemplary embodiment, timelines 72 and 85 allows a viewer to view full story of user's states. According to an exemplary embodiment, a more general view provide indications about specific areas of concern. The display of an exemplary embodiment depicted in FIG. 8A trains a user to have a full view of the story, from specific time points to a wider scene and from a wider scene to a full story (full lecture in an exemplary embodiment or even all the material being studied for a test or an exam). According to an exemplary embodiment, entire contents or lecture(s) can be viewed at the same time. As a result, the user may compare and evaluate progress by seeing different perspectives of the lecture.

Such that the timelines 71 and 88 are provided with $t_n$ being shown in the middle and a time bar with five minutes prior to the currently displayed time and five minutes after the currently displayed time are provided. Further, the timelines 72 and 85, generated by the timeline generator 61c, are displayed to the user and are the timelines for the entire cognitive state history along the entire lecture (entire content). The currently output position or video portion is shown as time $t_n$ and it is displayed with respect to the entire contents. According to an exemplary embodiment, timelines 72 and 85 are similar to video controls known in the art but with cognitive states of a user marked thereon.

FIG. 8A shows that the currently displayed image is approximately at the middle of the entire contents illustrated by the timelines 72 and 85. As shown in FIG. 8A, the user may be studying and/or reviewing the contents (lecture). Accordingly, the headset depicted in FIG. 1 may also be worn by the user during the review time. In an exemplary embodiment, additional sensory data generated during the review time is synchronized by the synchronizer 61a with the contents (video and audio) being displayed and the timeline(s) generator 61c may generate review timelines 85 and 88 which would depict the cognitive state of the user during the real-time of review. According to an exemplary embodiment, the cognitive state of the user in recent or current time (during the review time) is depicted in the timelines 85 and 88. The review timelines 85 and 88 maybe updated in real time and displayed to the user so that the understanding of the material during the review or studying process is easily comprehended by the user. According to an exemplary embodiment, the cognitive state 86 of the user in real time may be output on a display on the fly. Additionally, the synchronizer 61a may synchronize notes 87 taken by the user during the lecture (original presentation of the contents) and/or notes made during the review or study of the content, via a tool bar 89. According to an exemplary embodiment, correlations from insights may be retrieved, displayed, and edited by a user.

According to an exemplary embodiment depicted in FIG. 8A, the timelines 71, 72, 85, and 88 depict the cognitive state of the user. However, this is provided by way of an example and not by way of a limitation. According to various exemplary embodiments, only one timeline or a portion of the timelines may show the cognitive state of the user. For example, only timelines 72 and 85 may show the cognitive state of the user during the original lecture presentation and during review, respectively. Further, FIG. 8A depicts the cognitive state of the user using coloring or shading but this is provided by way of an example only and not by way of a limitation. One of ordinary skill in the art would readily appreciate that other markings, indicators, and coding techniques may be used to depict the cognitive state of the user. According to an exemplary embodiment, a user may scroll via any one of the timelines to navigate to needed portions in the contents. In an exemplary embodiment, by way on an example, a user may click or select a particular point on the timeline 72 or the timeline 85 and the UI will switch to a new screen using the selected point as point n.

Figure 8B:
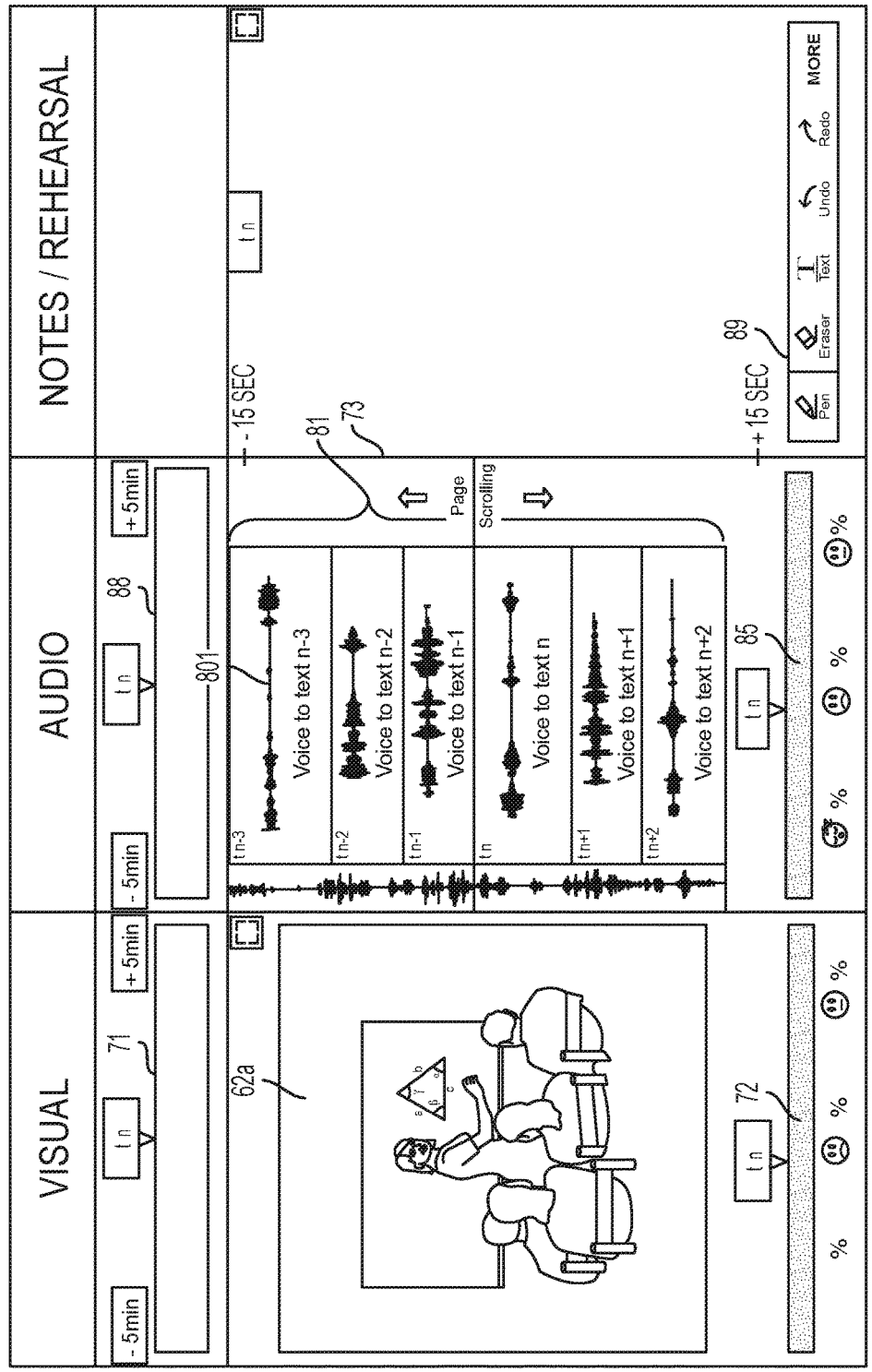

FIG. 8B is a view illustrating audio signals being displayed together with the text to enhance the ability of visible speech recognition, for example for a foreign language student, according to another exemplary embodiment. In FIG. 8B, in addition to the text 81 being displayed, audio data 801 is provided to allow the user to listen in addition to viewing the contents in a text format.

Figure 9A:
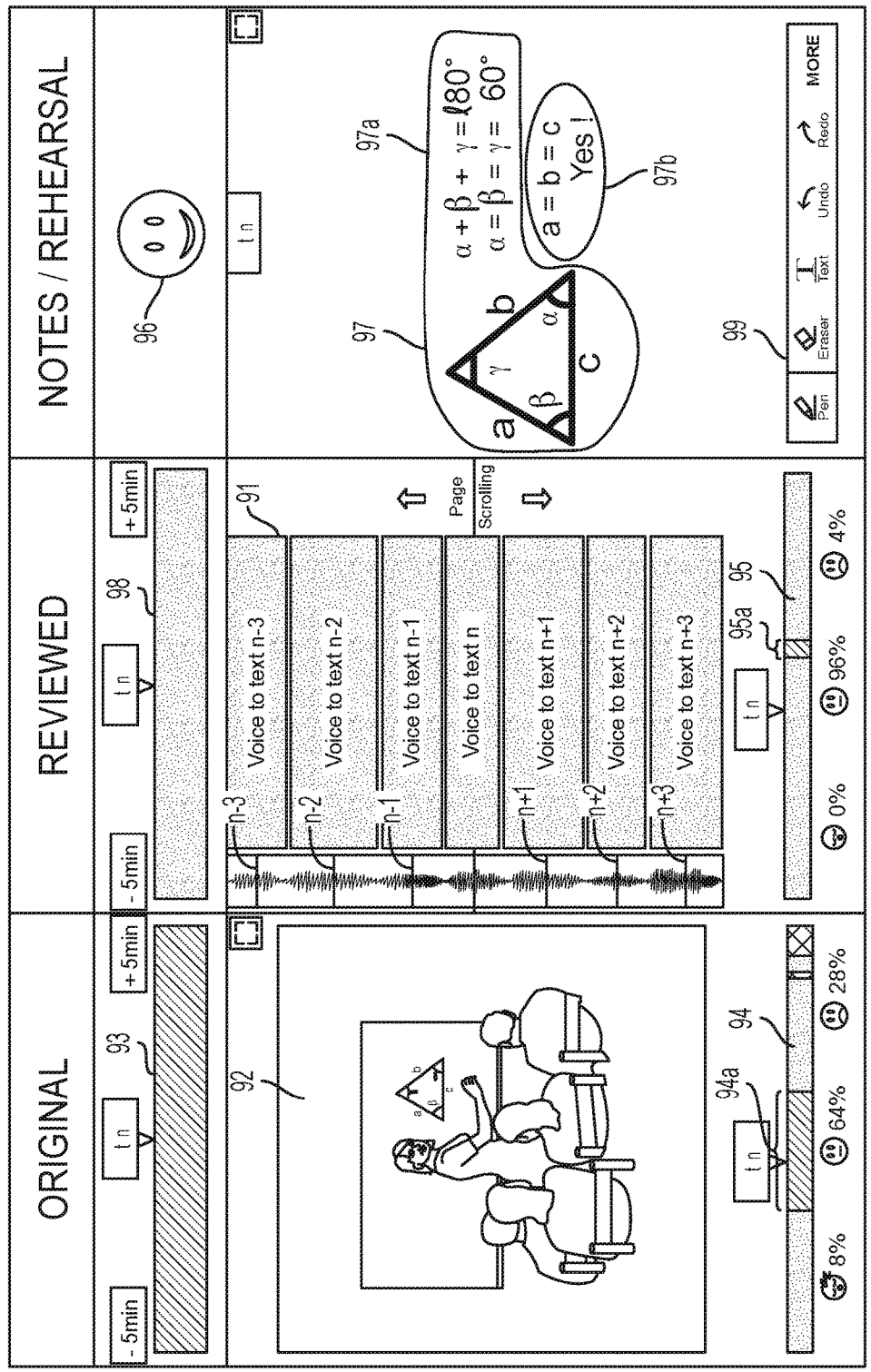
FIGS. 9A-9C are views illustrating methods of building correlations after studying contents, according to exemplary embodiments.

FIG. 9A is a view illustrating a method of building correlations after studying contents according to an exemplary embodiment.

As shown in FIG. 9A, after the user has reviewed the content, the timeline generator 61*c* updates the timelines 95 and 98 indicating that the cognitive state of the user is confident with a larger portion of the entire contents than prior to the review. For comparison, the timeline 94 shows that the user is confused with respect to a larger portion of the content 94*a* as opposed to after reviewing, the user is confused with respect to a smaller portion 95*a* depicted in the timeline 95. In FIG. 9A, the original content 92 is displayed with a timeline 93 being in a shade of color indicating that the user is confused as well as the timeline 94 showing a portion of the total contents that the user is confused to be about (28%) and indicated by a different shading portion 94*a*. After reviewing the contents, the user now understands most of the material or a significant portion of the material. After the review, the timeline 95 depicts the cognitive state of the user as confident and the converted text portions 91 are now depicted in a shade indicating confidence or user's understanding of the material/contents. The current state 96 of the user is also shown as confident. Combined notes 97 are shown to the user. The notes 97*a* made during the original presentation of contents and additional notes 97*b* made during the review or studying process are shown together, synchronized by the synchronizer 61*a* and may be further edited using the toolbar 99.

Figure 9B:
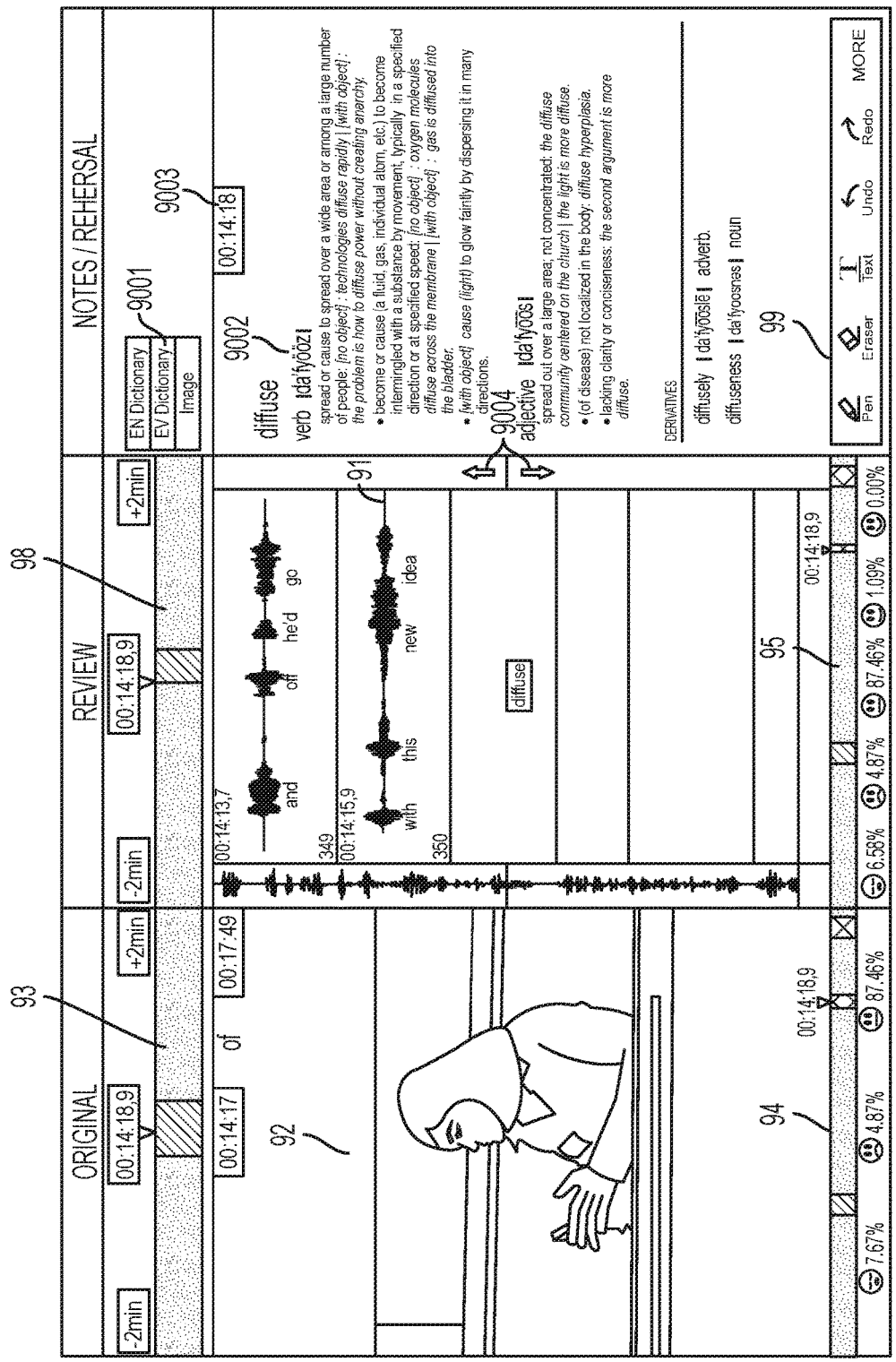

FIG. 9B is a view illustrating building correlations with support tools according to an exemplary embodiment. As shown in FIG. 9B, in addition to viewing the original contents 92 with timelines 93 and 94, the user is also provided with timelines 95 and 98, as explained above. Also, the user may be able to listen as well as view the words being spoken, as shown in the display of audio data 91. The user may also scroll the content using arrow keys 9004. By selecting or emphasizing a certain word in the audio data 91, the user may be provided with a definition in a view 9003. That is, in an exemplary embodiment, a view 9003 may include a search engine such as a dictionary 9001 or a tutorial (if a math concept is being studied for example). The type of a tutorial is depicted in a view 9001. In an example provided, an English dictionary or an image for the word may be provided. The definitions may be depicted in a notes section 9002. Additionally, a timely 9003 may be provided to explain where in the text the term is found. According to an exemplary embodiment, concepts and meanings of the lecture may be improved with the additional support tools such as tutorials and dictionaries.

Figure 9C:
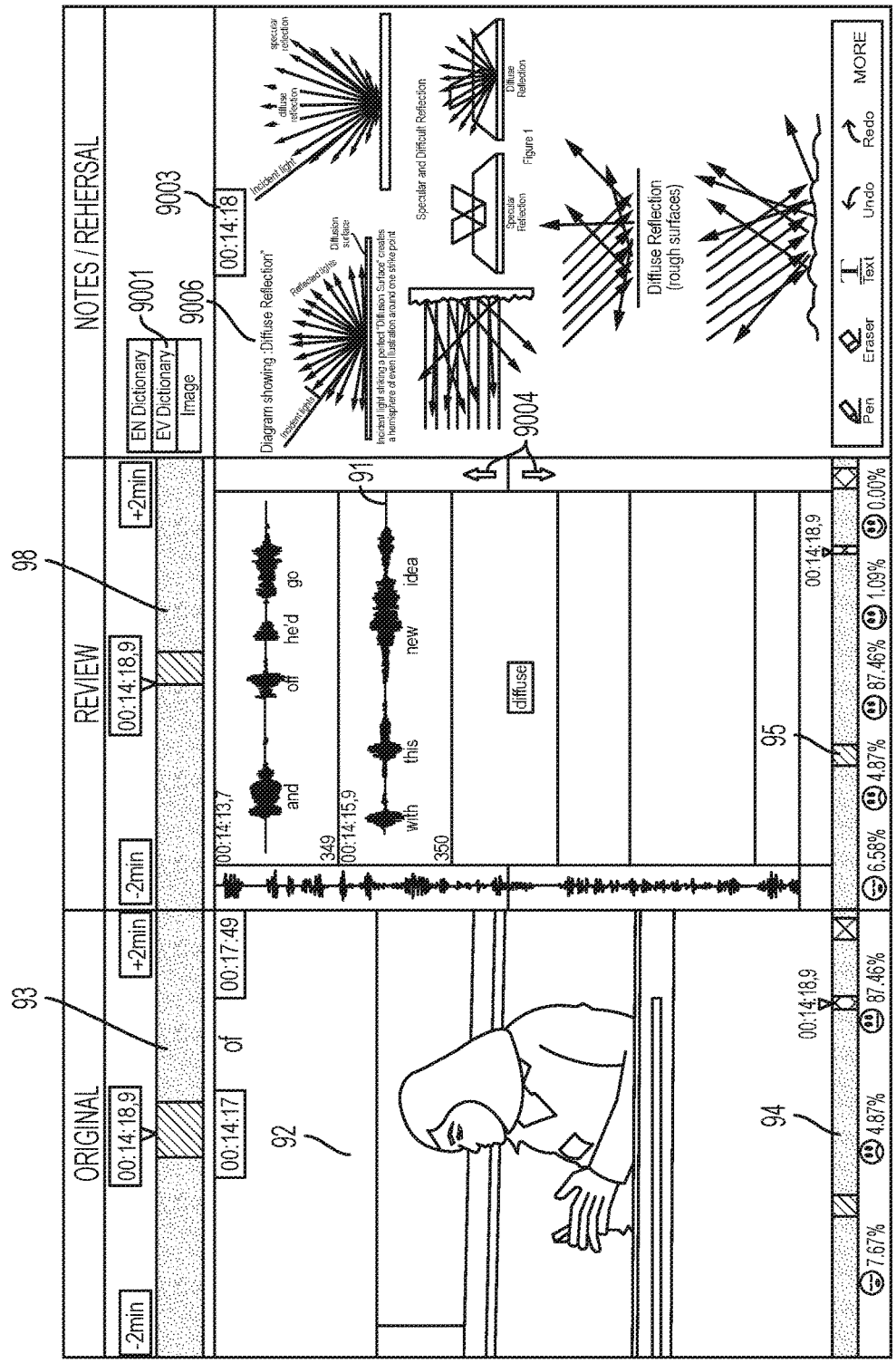

FIG. 9C is a view illustrating building correlations with support tools according to an exemplary embodiment. In FIG. 9C, in a tutorial depicted in a view 9001, image is selected and as such, images illustrating the concept is depicted in the notes section 9006. According to an exemplary embodiment, a method to enhance the ability of visible correlation building to support foreign students, for example, in understanding English, is provided. According to an exemplary embodiment, support tools are depicted as an image database and a definitions database. This is provided by way of an example and not by way of a limitation. According to an exemplary embodiment, other support tools may be provided including but not limited to textbooks, internet searches, and even related exercises and homework.

Figure 10:
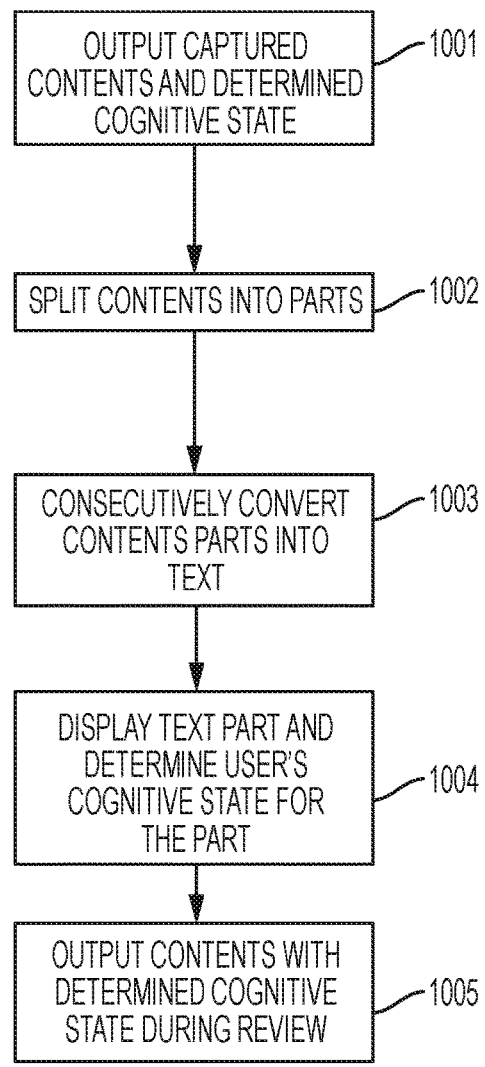
FIG. 10 is a flow chart illustrating a method of building correlations or an understanding of contents, according to an exemplary embodiment.

FIG. 10 is a flow chart illustrating a method of building correlations or an understanding of contents according to an exemplary embodiment.

As shown in FIG. 10, in operation 1001, the review apparatus retrieves from a memory captured contents and corresponding captured cognitive state. The captured contents may include video and/or audio data. The captured cognitive state of the user may include ET0-ET10, as explained in greater detail above. The determined cognitive state may be shown on one or more timelines corresponding to the viewed and/or listened contents. In operation 1002, the contents is split into content submodules (parts) based on time, semantic meaning, or as specified by the user e.g., into five second time intervals. The contents may be displayed to the user in parts as submodules. Audio contents is converted, part by part, consecutively, into text, in operation 1003. The cognitive state of the user during the review is determined with respect to the parts/submodules being output on a display and/or via a speaker, in operation 1004. In operation 1005, the cognitive state of the user with respect to the review material is generated and presented to the user. According to an exemplary embodiment, cognitive state of the user during the review is determined and output so that the user can determine his further understanding of the material.

Figure 11:
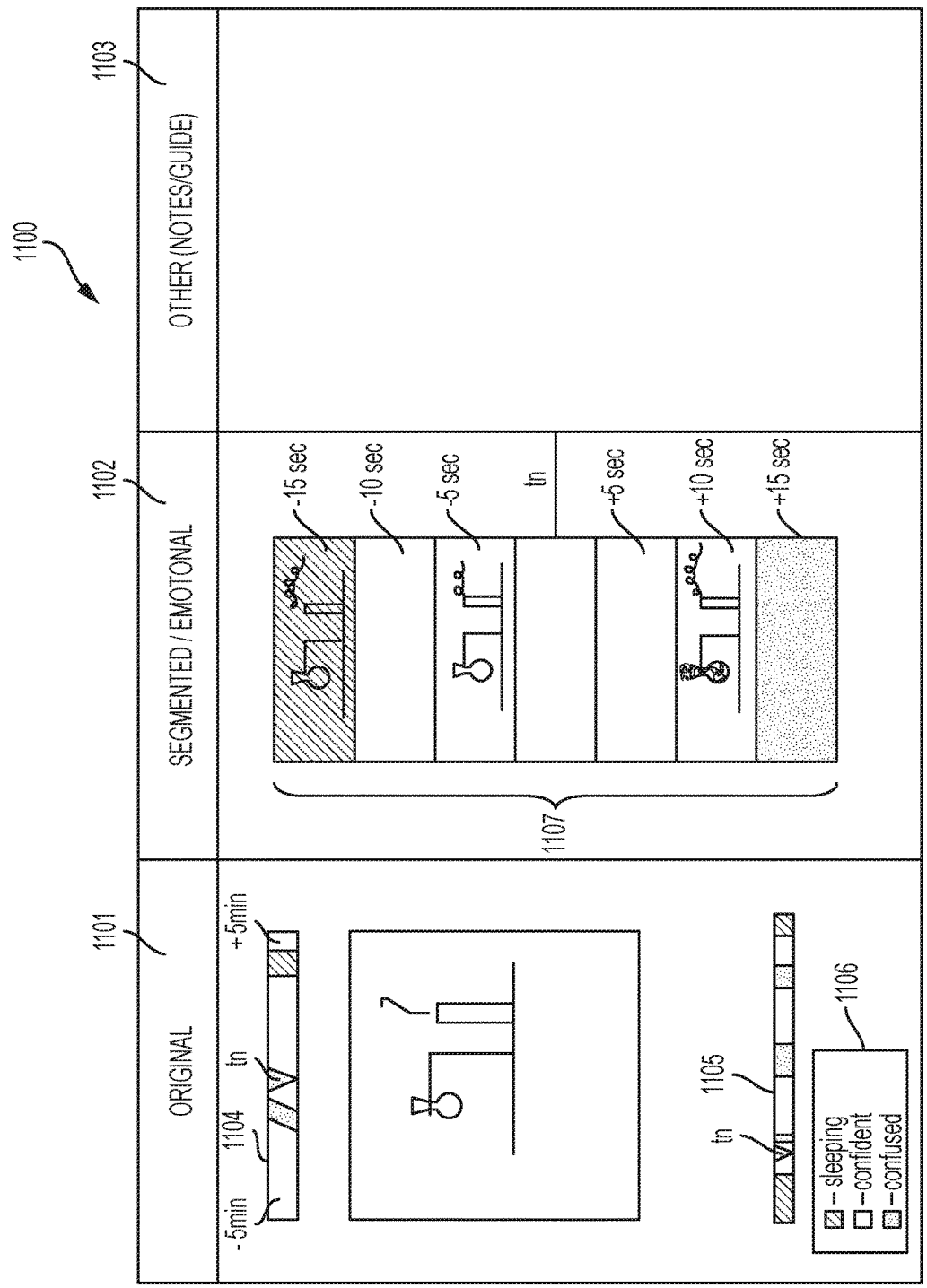
FIG. 11 is a view illustrating a method of building correlations according to yet another exemplary embodiment.

FIG. 11 is a view illustrating a method of building correlations according to yet another exemplary embodiment. As shown in FIG. 11, original data may be displayed in a first area 1101 of a screen 1100. The original data 1101 may include any one of video data and/or audio data recorded during a meeting, a conference, an experiment, a sport exercise, and so on. In an exemplary embodiment depicted in FIG. 11, the original data 1101 is video data (without audio data) that is recorded during a laboratory class such as a chemistry experiment. The timelines 1104 and 1105 are similar to the timelines described above and are not further described here to avoid redundancy. As shown in FIG. 11, a key map 1106 is provided indicating cognitive state of the user with respect to the shading technique used in the timeline 1105. Although only timeline 1105 is shown shaded with emotional state of the user, one of ordinary skill in the art would readily appreciate that the timeline 1104 may also be shaded with the cognitive state of the user.

The segmented data is provided in a second area 1102 of the screen 1100. According to an exemplary embodiment, the original data 1101 may be segmented according to a predetermined criteria. By way of an example, the video data may be segmented into a predetermined chunks of five seconds intervals, by way of an example. One of the frames such as a first frame, a last frame, one of the frames in the middle may be used as an icon or image for a respective segment. In FIG. 11, data segments 1107 are provided which respectively correspond to five seconds of video data. By clicking on each of the plurality of segments, the user may view the respective video segment. The segments are shaded according to the cognitive or emotional state of the user. In FIG. 11, a third area 1103 of the screen 1100 may include user notes, professor notes, textbook links, internet links, guides, dictionaries, and tutorials regarding the original data. Accordingly, various data types are segmented or split into parts based on various criteria. For example, the data may be split into parts based on time intervals (each five seconds). According to another exemplary embodiment, the meaning of the data may be analyzed and the data may be split into portions using speech pauses or image recognition techniques that would recognize a scene change. These are provided by way of an example and not by way of a limitation.

Figure 12:
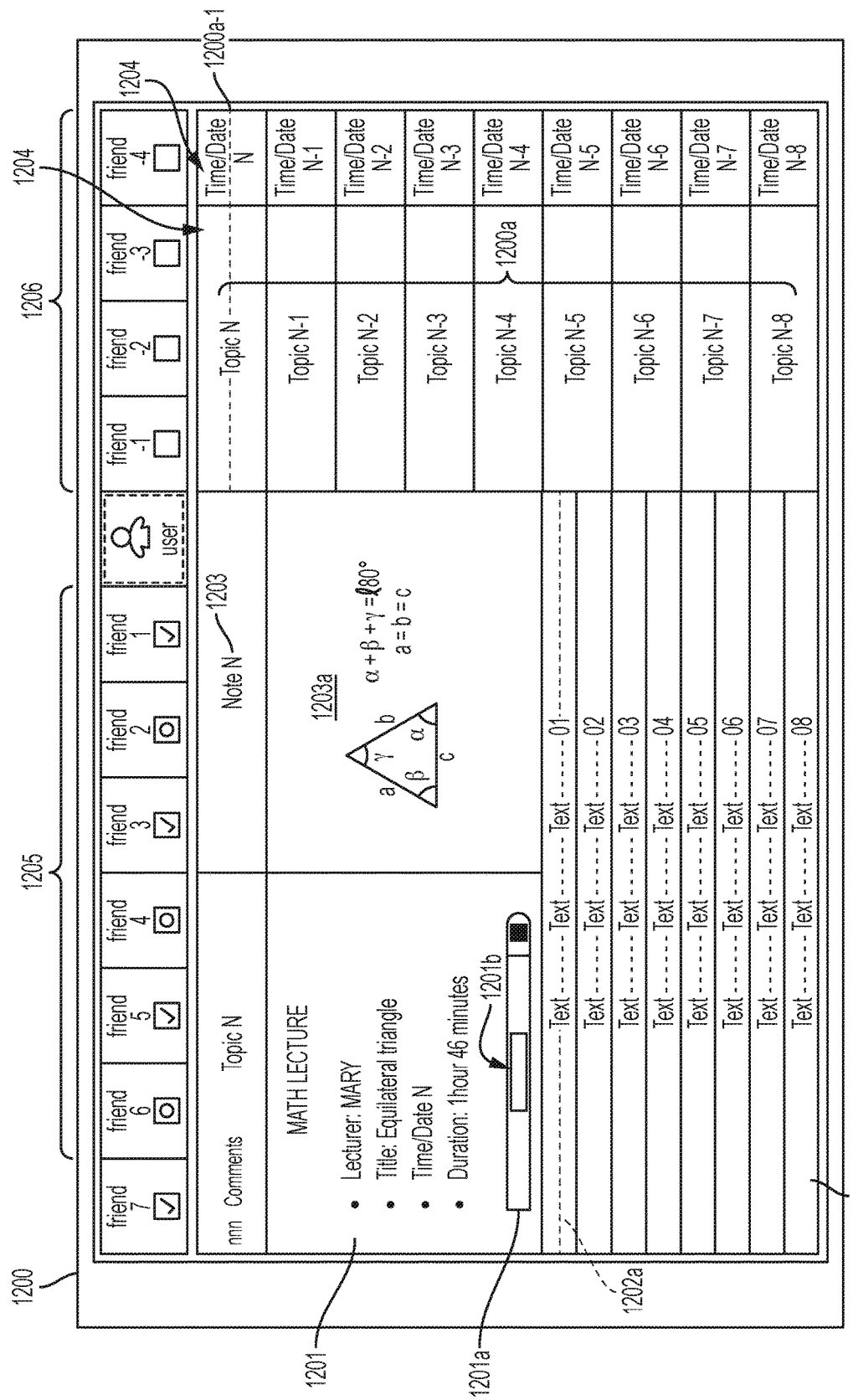
FIGS. 12 and 13 are views illustrating a method of building correlations via a group setting according to yet another exemplary embodiment.

According to yet another exemplary embodiment, the learning process is further enhanced via group learning. For example, a social networking application feature is provided to enhance the learning process. FIG. 12 is a view illustrating a user home page of a social networking application according to an exemplary embodiment. In an exemplary embodiment, a social networking application similar to Facebook or Twitter is utilized to enhance the learning process.

As shown in FIG. 12, a user home screen 1200 is displayed to a user via a mobile device such as a smart telephone for example. In the user's home page screen 1200, a list of lectures stored in user's database 1200a are displayed. The list is accompanied by a timeline 1200a-1 indicating when the lecture topic was obtained. For example, as shown in FIG. 12, a list of lecture topics 1200a includes lecture topics N, N−1, N−2, . . . N−8. These lectures have a corresponding time in which they were acquired. As shown in FIG. 12, lecture topic N was obtained at time/date N, as shown in the timeline 1200a-1. The lecture topic N−1 was obtained at a time/date N−1, as also shown in the timeline 1200a-1 and so on. The lecture topic N is at a currently position of the timeline (top position) which indicates the currently studied lecture topic. The topic N is summarized on the left portion 1201 of the home screen page 1200. According to an exemplary embodiment depicted in FIG. 12, the topic N is a math lecture where Mary is the lecturer of the topic with the length of the lecture being 1 h 46 minutes and recorded on time/date N. That is, in an exemplary embodiment, the left portion 1201 of the home screen page 1200 provides metadata about the current lecture topic i.e., topic N. Additionally, according to an exemplary embodiment, a timeline 1201a is provided with respect to the lecture topic N. The timeline 1201a shows the confidence levels at various portions of the lecture topic N. The user may review the script of the lecture topic N, as shown in a lower portion 1202 of the user's home page screen 1200. That is, the lower portion 1202 shows the lecture topic N converted to text. The top text module 1202a corresponds to the current position of the lecture topic N that the user is currently reviewing, as indicated by the current position indicator 1201b on the timeline 1201a. According to an exemplary embodiment, the user can use the timeline 1201a to scroll to a desired portion in the script 1202. The user can review the lecture topic N without load the video of the lecture topic N by scrolling the timeline 1201a or by scrolling through the text modules 1202. The user home page screen 1200 further includes a notes section 1203 for displaying user notes corresponding to the lecture topic N. In an exemplary embodiment, the notes section 1203 will display user's notes input during the review and/or during the original lecture based on a current portion of the lecture topic N being reviewed. In other words, the notes section 1203 is synchronized with the current position indicator 1201b on the timeline 1201a and with the current text module being review 1202a. The notes section 1203 may present notes made during the original lecture, during the review, and/or both depending on user defined settings. Default settings would provide for displaying all available notes corresponding to the current position indicator 1201b.

When the user wants to view the features or metadata about the next topic, the user scrolls the list 1200a up/down, and the areas 1201, 1202, and 1203 will provide the contents of topic corresponding to the lecture topic on top of the list.

Additionally, as shown in FIG. 12, the home screen 1200 includes a display component or a display element for the friends of the user. In an example, depicted in FIG. 12, friends 1-7 are shown in the display area 1205 and friends −1, −2, −3, and −4 are shown in the display area 1206. As shown in FIG. 12, friends with no new posts are shown in the display area 1205 and friends with new posts i.e., the ones that the user has not yet seen are shown in the display area 1206. The user has commented on the posts of the friends 3, 5, 7, which is reflected with a display indicator such as a checkmark and the user has not commented on the posts of the friends 2, 4, and 6, which may be visible via another indicator such as an unchecked box.

In an exemplary embodiment, the posts are topic specific such that by viewing a particular topic, the screen will display posts corresponding to the topic and/or indicate friends that have comments on the particular topic. In an exemplary embodiment, the user may swipe an icon of a friend to view one or more posts of that friend.

Figure 13:
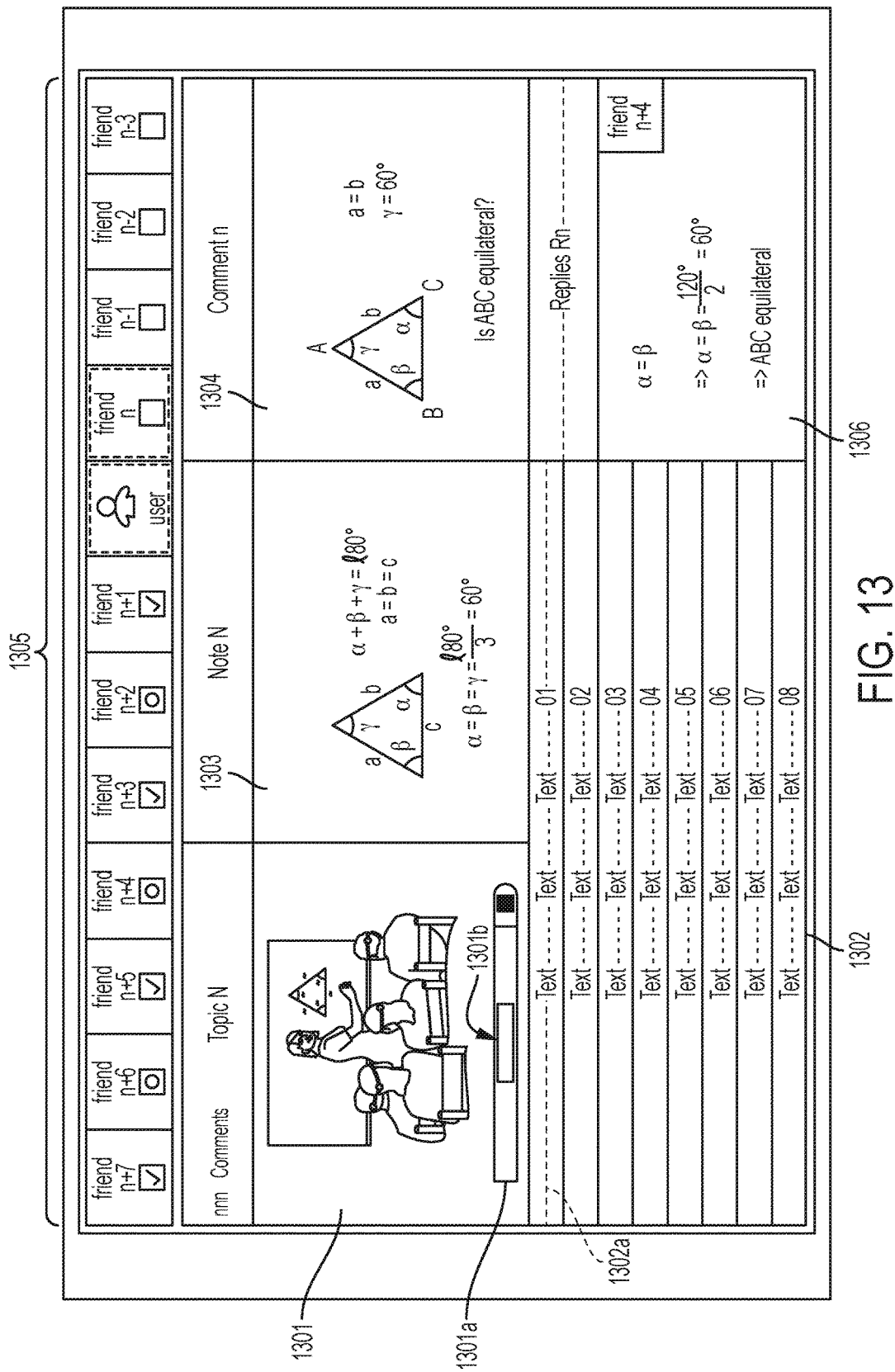

As shown in FIG. 13, the user selects a lecture topic N and the lectute topic N is depicted in the area 1301 in a form of a video, according to an exemplary embodiment. Additionally, in the area 1301, a timeline 1301a may be displayed. That is, according to an exemplary embodiment, when a user selects any point on the 1200a portion of the user home page screen depicted in FIG. 12, the video of the lecture topic N will play at a screen portion 1301, as shown in FIG. 13. The user can pause/play video at any time by touching an area 1301, 1302, or 1303. The user can fast forward, rewind the video of the lecture topic N by scrolling 1302 or by manipulating the timeline of 1301a. During playing of the video of the lecture topic N, the user can view the notes made by her and additionally notes made by friends and comments of the friends by manipulating screen section 1305.

As depicted in FIG. 13, the audio of the video of the lecture topic N played in the area 1301 is converted into text and displayed in the area 1302. In the area 1303, user notes (including friends' notes depending on user settings and/or default settings) are displayed. In the area 1304, comments made by a user (including friends' comments depending on user settings and/or default settings) are displayed. For example, friends n, n−3, n+1, n+3, n+5, n+7 may have comments that are directed to the current portion 1302a of the lecture topic N, as indicated in a section 1305 via a display indicator of a checkmark, provided by way of an example only and not by way of a limitation. Additionally, an area with replies 1306 may be provided. In an exemplary embodiment depicted in FIG. 13, friend n−1, n−2, n+2, n+4, and n+6 may have comments on comments of user's friend (replies). In an exemplary embodiment, user comments displayed in the area 1304 may be a mathematical problem given by the lecturer during class to be solved at home. As such, in an exemplary embodiment, replies from friends displayed in an area 1306 may include a solution to the problem and the user may check various solutions of his friends by reviewing the replies Rn provided in the area 1306 of the lecture topic N screen depicted in FIG. 13.

According to an exemplary embodiment, a user may browse through comments/replies of various friends by selecting a friend in the friend display area 1305. By selecting one or more friends in the friend display area 1305, the user will see the replies/comments made by the selected friends in the area 1306. This is provided by way of an example and not by way of a limitation.

Figure 14:
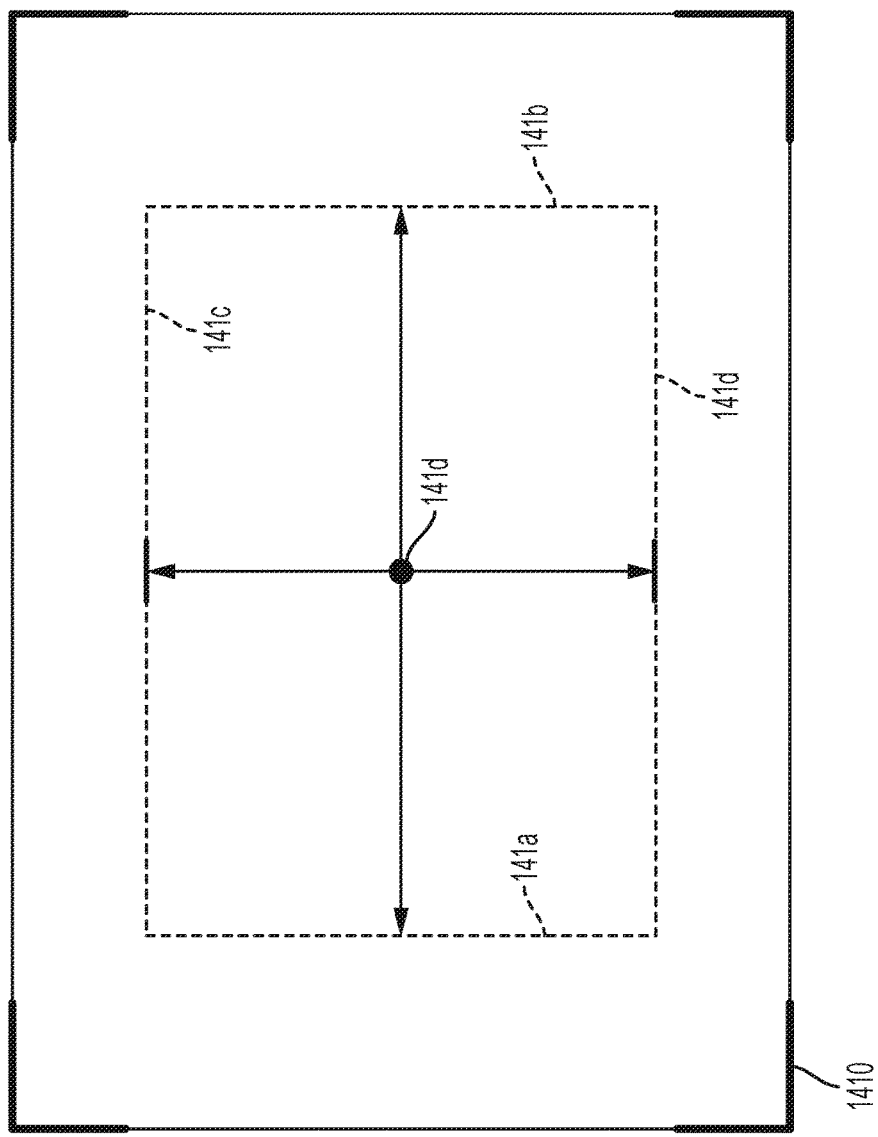
FIG. 14 is a view illustrating a method of determining a skill level of a user with respect to a particular task according to yet another exemplary embodiment.

FIG. 14 is a view illustrating a method of determining a skill level of a user with respect to a particular task according to yet another exemplary embodiment.

As shown in FIG. 14, a reference frame 1410 of images captured by a camera such as a camera on a headset 1, described above with reference to FIG. 1, may be used to determine motion of an object 141. In the reference frame 1401, a stationary object 141 may be displayed in the center. That is, according to an exemplary embodiment, the stationary object 141 may be an object that the user is looking at such as a golf ball (when the user is playing golf), a point on the blackboard (when the user is in a classroom), or a soccer ball (when the user is playing soccer). These stationary objects are provided by way of an example and not by way of a limitation. Base on analyzing a plurality of captured images, the motion of the object 141 inside the frame 1410 is detected. By analyzing the motion of the object 141 inside the frame 1410, an emotional state of the user may be detected. For example, the detected motion of the object 141 reflects the motion of the forehead of user, which may reflect the user's cognitive state. According to an exemplary embodiment, the detection method may detect additional emotional/cognitive information of the user to set aside the noise influence in the EEG signals.

In an exemplary embodiment, a horizontal motion of the user's head is detected if the stationary object 141 is moved from the center in the directions 141a and 141b. Additionally, a vertical motion of the user's head is detected if the stationary object 141 is moved from the center in the directions 141c and 141d, as shown in FIG. 14. The motion is detected by analyzing a subset of image frames i.e., a portion of the video. As explained in greater detail above, a portion of the video may correspond to the chunks or split up blocks, described above with reference to the text to speech conversion.

According to yet another exemplary embodiment, the portion of the video used to determine motion may be context specific.

For example, if the user is looking at a particular point on a black board, the motion of the user shaking his head or nodding his head may be detected. That is, detected horizontal motion may indicate that the user is shaking his head and is thus, appear to be confused. On the other hand, detected vertical motion of the head may indicate that the user understands the material being presented. As such, the portion of the video to be used as a reference set will depend on the detected motion of the user's head i.e., until a pause for example.

According to yet another exemplary embodiment, the portion of the video to be used to detect the motion may depend on a task being performed. If the user is playing golf, the motion may help detect the quality of a task. For example, when the golfer is putting, the object 141 should remain stationary inside the reference frame 1410 throughout the putting process. If the putting was a fail, the golfer can review and view that the stationary object 141 moved down, and the user can thus determine that he was heading up during his putting. By analyzing his motion during the putting process, his putting may be improved.

Figure 15:
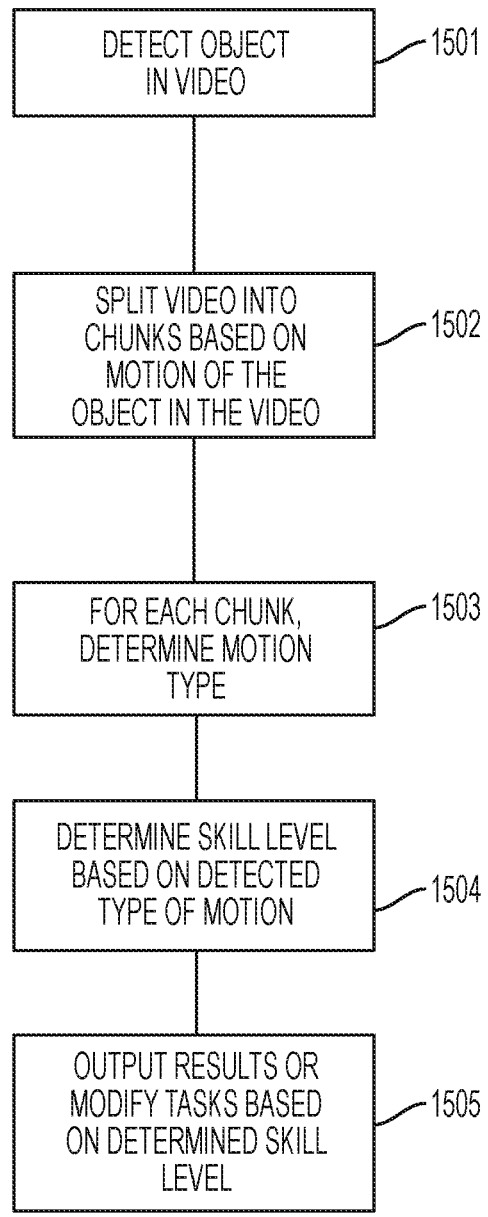
FIG. 15 is a flow char illustrating a method of determining a skill level of a user with respect to a particular task according to yet another exemplary embodiment.

FIG. 15 is a flowchart illustrating a method of determining a skill level of a user with respect to a particular task according to an exemplary embodiment described above with reference to FIG. 14.

As shown in FIG. 15, in operation 1501, a stationary object is detected. In an exemplary embodiment, a stationary object may be detected by using a variety of image recognition techniques known in the art such as a center point of where the user is looking such as a golf ball or a blackboard. In operation 1502, divide a video into chunks or segments based on a motion detected with respect to the stationary object. According to an exemplary embodiment, the video is analyzed to determine motion of the stationary object from image frame to image frame. Each motion may be determined to be a chunk of a segment of the video. For each determined chunk or segment, the type of motion is determined in operation 1503. The type of motion being determined is based on a context.

For example, with respect to the blackboard example, the type of motion being detected maybe horizontal or vertical motions that would indicate whether the user is confused (shaking his head) or is confident (nodding his head). With respect to the golf example, the type of motion being detected may be the movement of the head with respect to the golf ball and the timing from the beginning of the movement until the golf ball is hit.

In operation 1504, a skill level or confidence level of the user is determined based at least in part on the determined type of motion. For example, if the user is nodding his head and the sensory data indicates that the user's cognitive state is confident, these factors can be combined to determine that the user knows and understands the materials being presented. On the other hand, if the user's swing is determined to be slow (taking a long time) and the golf ball is moving from frame to frame, these factors can be combined with sensory data (which may indicate that the user's memory is working hard) to determine low skill level. Expert golfer would mostly utilize his motor skills as opposed to memory skill, swing fast, and keep his eyes on the ball, for example.

In an exemplary embodiment, the determined skill level may be output to a user or operations may be modified based on the determined skill level in operation 1505. According to an exemplary embodiment, additional tutorials or materials may be presented to the user based on the determined skill level. As an alternative, the lecture may be presented at a slower speed with additional pauses. According to yet another exemplary embodiment, a golf game may be color coded to indicate that the user needs further practice with respect to a particular hole, a particular motion, a task, and so on. The user may be directed to a certain area within the course to practice a particular task.

According to yet another exemplary embodiment, when a complex task is being performed (e.g., operating a complex machinery or equipment), the determined skill level may be used to output alarms or even shut down the equipment if the skill level is inadequate or if it appears that the user is falling asleep, for example.

According to an aspect of exemplary embodiments, a personal intuition-based cognitive assistant system is provided, which includes: one or more apparatuses configured to capture data from an environment comprising synchronized visual and audio information, at least one sensor configured to capture intuitive state or cognitive state of a user corresponding to the synchronized visual and audio information captured from environment and observed, listened by the user; at least one display apparatus configured to display captured cognitive information and processed cognitive information comprising captured synchronized visual, audio information, captured user's intuitive state information and processed synchronized visual, audio information and processed user's intuitive state information. The apparatus further includes a processor configured to: identify the distinctive intuitive states of the user based on the captured intuitive states or sensory data and the distinctive reference signals stored in a database, interpret the identified distinctive intuitive states of the user into identified distinctive visible intuitive marks, interpret the captured synchronized audio information into synchronized text and symbols, chunk the serial of interpreted synchronized text and symbols into separated consecutive synchronized subtitle modules, divide continuous captured synchronized visual and audio information into discrete consecutive synchronized videos in corresponding to consecutive synchronized subtitle modules, and a display, which displays separated consecutive synchronized subtitle modules in separate consecutive subtitle sub-windows within a script window. The processor is further configured to mark synchronized subtitle windows with the synchronized identified distinctive visible intuitive marks in corresponding to the identified distinctive intuitive states of the user. The apparatus further includes a memory which stores the synchronized cognitive information including captured synchronized visual, audio, intuitive information, processed synchronized visual, audio, intuitive information.

According to various exemplary embodiment, a user may readily appreciate topics that require further attention when studying, face-to-face meeting, video telephonic conversation and so on. According to various exemplary embodiment, personalized notes and comments made, thoughts formed based on environment observed and listened by the user can be synchronized with the environment. These personalized conversational documents, thoughts may mimic the learning and the thoughts of the user's working memory. They are documented then they are stored, output, shared to assist the user in making various kinds of "post-conversation" information store and exchange. The output may take various forms including email, social media, and so on.

The descriptions of the various exemplary embodiments have been presented for purposes of illustration, but are not intended to be exhaustive or limited to the embodiments disclosed.

Many changes may be apparent to those of ordinary skill in the art without departing from the scope and spirit of the described embodiments. The terminology used herein was chosen to best explain the principles of the embodiments, the practical application or technical improvement over technologies found in the market place or to enable ordinary skill in the art to understand the embodiments disclosed herein.

In an exemplary embodiment, the cognitive module processor may be implemented on a tangible computer-readable medium. The term "computer-readable medium" as used herein refers to any medium that participates in providing instructions to a processor for execution. A computer readable medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable medium would include the following: an electrical connection having two or more wires, a portable computer diskette such as a floppy disk or a flexible disk, magnetic tape or any other magnetic medium, a hard disk, a random access memory (RAM), a read-only memory (ROM), an erasable programmable read-only memory (EPROM or Flash memory), a memory card, any other memory chip or cartridge, an optical fiber, a portable compact disc read-only memory (CD-ROM), any other optical medium, punchcards, papertape, any other physical medium with patterns of holes, or any other medium from which a computer can read or suitable combination of the foregoing.

In the context of this document, a computer readable medium may be any tangible, non-transitory medium that can contain, or store a program for use by or in connection with an instruction execution system, apparatus, or device.

Another form is signal medium and may include a propagated data signal with computer readable program code embodied therein, for example, in a base band or as part of a carrier wave. Such a propagated signal may take any of a variety of forms, including, but not limited to, the electromagnetic, optical, or any suitable combination thereof. The signal medium may include coaxial cables, copper wire and fiber optics, including the wires that comprise data bus. The signal medium may be any medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc. or any suitable combination of the foregoing.

Computer program code for carrying out operations for aspects of the exemplary embodiments may be written in any combination of one or more programming languages, including an object oriented programming language such as Java, Smalltalk, C++, .Net or the like and conventional procedural programming languages. The program code may execute entirely on the user's computer, partly on the user's computer, as a stand-alone software package, partly on the user's computer and partly on a remote computer or entirely on the remote computer or server. The remote computer may be connected to the user's computer through any type of network, including a local area network (LAN) or a wide area network (WAN), or the connection may be made to an external computer (for example, through the Internet using an Internet Service Provider).

The computer-readable medium is just one example of a machine-readable medium, which may carry instructions for implementing any of the methods and/or techniques described herein. Such a medium may take many forms, including but not limited to, non-volatile media and volatile media. Non-volatile media includes, for example, optical or magnetic disks. Volatile media includes dynamic memory.

Various forms of computer readable media may be involved in carrying one or more sequences of one or more instructions to a processor such as a CPU for execution. For example, the instructions may initially be carried on a magnetic disk from a remote computer. Alternatively, a remote computer can load the instructions into its dynamic memory and send the instructions over a telephone line using a modem. A modem local to a computer system can receive the data on the telephone line and use an infra-red transmitter to convert the data to an infra-red signal. An infra-red detector can receive the data carried in the infra-red signal and appropriate circuitry can place the data on the data bus. The bus carries the data to the volatile storage, from which processor retrieves and executes the instructions. The instructions received by the volatile memory may optionally be stored on persistent storage device either before or after execution by a processor. The instructions may also be downloaded into the computer platform via Internet using a variety of network data communication protocols well known in the art.

The flowchart and block diagrams in the Figures illustrate the architecture, functionality, and operation of possible implementations of systems, methods and computer program products according to various exemplary embodiments. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or two blocks may sometimes be executed in the reverse order, depending upon the functionality involved. It will also be noted that each block of the block diagram and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology as used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or acts for performing the function in combination with other claimed elements as specifically claimed.

The description of the exemplary embodiments has been presented for purposes of illustration and description, but is not intended to be exhaustive or limiting in any form. Many modifications and variations will be apparent to those of ordinary skill in the art without departing from the scope and spirit of the invention. Exemplary embodiments were chosen and described in order to explain operations and the practical applications thereof, and to enable others of ordinary skill in the art to understand various embodiments with various modifications as are suited to the particular use contemplated. That is, various modifications to these embodiments will be readily apparent to those skilled in the art, and the generic principles and specific examples defined herein may be applied to other embodiments without the use of inventive faculty. For example, some or all of the features of the different embodiments discussed above may be combined into a single embodiment. Conversely, some of the features of a single embodiment discussed above may be deleted from the embodiment. Therefore, the present disclosure is not intended to be limited to exemplary embodiments described herein but is to be accorded the widest scope as defined by the features of the claims and equivalents thereof.

What is claimed is:

1. A personal emotion-based cognitive assistant system comprising:
   at least one apparatus, which is worn by a user and is configured to capture, from an environment, data comprising synchronized visual and audio information, wherein the visual information is the environment viewed by the user and the audio information is the environment heard by the user;
   at least one sensor configured to capture emotional state of the user synchronized with the data captured by the apparatus;
   a review apparatus comprising a memory and a processor, wherein the processor is configured to:
      divide the data captured by the apparatus into a plurality of segments according to a predetermined criteria,
      for each of the plurality of segments, determine an intuitive state of the user, comprising a type of correlations and a level of correlations, generated from a comparison between predetermined components of the emotional state of the user captured by the sensor which corresponds to the respective segment, from among the plurality of segments, and distinctive reference signals stored in the memory, wherein the distinctive reference signals represent distinctive intuitive reference samples,
      generate at least one timeline, and
      control to display the generated timeline comprising an emotional indicator for each of the plurality of segments, wherein the emotional indicator indicates the determined intuitive state of the user,
   wherein the data comprises said visual information and said audio information synchronized with each other,
   wherein the review apparatus further comprises:
      a display configured to display the timeline and sequentially display the video information, and
      a speech to text converter configured to convert the audio information of the plurality of segments into synchronized text and symbols, wherein the audio information is divided into the plurality of segments based on pause point or based on whether a predetermined length is reached,
   wherein the processor generates a plurality of display elements, each of the plurality of display elements comprises a respective segment from among the plurality of segments and corresponding text converted by the speech to text converter, and
   wherein the display is further configured to display at least some of the generated plurality of display elements.

2. The personal emotion-based cognitive assistant system according to claim 1, wherein the display displays at least two display areas comprising:
   a first area in which the captured video information is played, and
   a second area in which the at least some of the generated plurality of display elements are displayed, wherein said at least some of the generated plurality of display elements comprise a current display element which corresponds to a portion of the video currently played in the first area, at least one display element from among the plurality of display elements that precede the current display element and at least one display element from among the plurality of display elements that follow the current display element, and wherein each of the plurality of the display elements comprise at least one of a mark and shading, indicating the determined intuition state of the user with respect to the respective display element from among the plurality of display elements.

3. The personal emotion-based cognitive assistant system according to claim 2, wherein the display apparatus further comprises a user input interface configured to receive user input, and wherein, in response to the user input received via the user input interface indicating a selection of a display element from among the plurality of display elements, the processor sets the selected display element as the current display element and determines at least the one display element that precede the current display element and at least one display element that follow the current display element and the display displays the current display element, said determined at least one previous display element and at least one future display element.

4. The personal emotion-based cognitive assistant system according to claim 3, wherein the processor is further configured to controls the display to execute at least one of a scroll function and a zoom function with respect to the plurality of display elements based on user input received via the user input interface.

5. The personal emotion-based cognitive assistant system of claim 3, wherein the review apparatus is further integrated with an inputter configured to provide sketching, inserting, and noting of correlations and rehearsals by the user, which are synchronized with the display elements displayed in the second area which is a central window on the display.

6. The personal emotion-based cognitive assistant system of claim 3, wherein the processor is further configured to search, retrieve, and insert at least one of images, graphs, texts, and sketches into a third area of the display, which comprises the at least one of images, graphs, texts, and sketches are related to the current display element.

7. The personal emotion-based cognitive assistant system according to claim 1, wherein the apparatus is a video camera worn on a head of the user, wherein the processor of the review apparatus is further configured to:
detect a stationary object in a plurality of images of the visual information captured by the video camera,
detect a motion of the detected stationary object in a border edge of a reference frame and based on the plurality of images, and
detect a cognitive or emotional state of the user based on the detected motion,
wherein the generated timeline comprises the detected cognitive or emotional state of the user, and
wherein the detected motion of the stationary object indicates that the user is performing a task.

8. The personal emotion-based cognitive assistant system according to claim 1,
wherein the review apparatus further comprises:
a motion to sketch converter configured to convert emotional motion information of the plurality of segments into synchronized sketch and symbols, wherein the emotional motion information is divided into the plurality of segments based on pause point or based on whether a predetermined length is reached,
wherein the plurality of display elements further comprise a respective segment from among the plurality of segments and corresponding sketch and symbols converted by the motion to sketch converter.

9. The personal emotion-based cognitive assistant system according to claim 1, wherein the processor is further configured to control the display to display a plurality of friends of a social networking services to which the user is subscribed.

10. The personal emotion-based cognitive assistant system according to claim 9, wherein the processor is further configured to control the display to display at least one comment by at least one of the plurality of friends with respect to one of the plurality of segments.

11. A personal emotion-based cognitive assistant method comprising:
receiving, by a computer, data comprising at least one of visual information and audio information captured from environment via at least one apparatus that is worn by a user, wherein the visual information is the environment viewed by the user and the audio information is the environment heard by the user;
receiving, by the computer, an emotional state of the user corresponding to the data captured by at least one sensor;
dividing, by the computer, said data into a plurality of segments according to a predetermined criteria,
for each of the plurality of segments, determining, by the computer, an intuitive state of the user comprising a type of correlations and a level of correlations, generated from a comparison between predetermined components of the received emotional state of the user which corresponds to the respective segment, from among the plurality of segments, and a plurality of distinctive reference signals stored in a memory, wherein the distinctive reference signals represent distinctive intuitive reference samples,
generating, by the computer, at least one timeline for the data, wherein the at least one timeline comprises an emotional indicator for each of the plurality of segments, which indicates the determined intuitive state of the user, and
outputting, by the computer, the generated timeline and at least a portion of the received data,
wherein the data comprises the visual information and the audio information synchronized with each other,
wherein the outputting comprising display the generated timeline and sequentially displaying the video information, and
wherein the method further comprises:
converting the synchronized visual and audio information of the plurality of segments into at least one of synchronized text, sketches, and symbols, wherein the synchronized visual and audio information is divided into the plurality of segments based on pause point or based on whether a predetermined length is reached,
generating a plurality of display elements, each of the plurality of display elements comprises a respective segment from among the plurality of segments and corresponding converted at least one of text, sketch, and symbols, and
displaying at least some of the generated plurality of display elements.

12. The personal emotion-based cognitive assistant method according to claim 11, wherein:
the displaying comprises displaying at least two display areas,
a first area in which the captured video information is played, a second area in which the at least some of the generated plurality of display elements are displayed, said at least some of the generated plurality of display elements comprise a current display element which corresponds to a portion of the video currently played in the first area, at least one display element from among the plurality of display elements that precede the current display element, and at least one display element from among the plurality of display elements that follow the current display element, and each of the plurality of the display elements comprise at least one of a mark and shading, indicating the determined intuitive state of the user with respect to the respective display element from among the plurality of display elements.

13. The personal emotion-based cognitive assistant method according to claim 12, further comprising receiving user input via a user input interface, wherein, in response to the received user input indicating a selection of a display element from among the plurality of display elements, setting the selected display element as the current display element and determining at least the one display elements that precede the current display element and at least one display element that follow the current display element and displaying the current display element, said determined at least one previous display elements, and at least one future display elements.

14. The personal emotion-based cognitive assistant method according to claim 13, further comprising executing at least one of a scroll function and a zoom function with respect to the plurality of display elements based on the received user input.

15. The personal emotion-based cognitive assistant method of claim 14, further comprising receiving at least one of sketching and noting of correlations and rehearsals input from the user, which are synchronized with the display elements displayed in the second area which is a central window on the screen.

16. A non-transitory computer readable recording medium storing therein a personal emotion-based cognitive assistant method, which when executed by a computer causes the computer to:

receive data comprising at least one of visual information and audio information captured from environment being observed by a user via at least one apparatus being worn by the user, wherein the visual information is the environment viewed by the user and the audio information is the environment heard by the user, wherein said visual information and said audio information is synchronized with each other;

receive an emotional state of the user corresponding to the data captured by at least one sensor;

divide said data into a plurality of segments according to a predetermined criteria;

for each of the plurality of segments, determine an intuitive state of the user comprising a type of correlations and a level of correlations, generated from a comparison between predetermined components of the received emotional state of the user which corresponds to the respective segment, from among the plurality of segments, and a plurality of distinctive reference signals stored in a memory, wherein the distinctive reference signals represent distinctive intuitive reference samples, generate at least one timeline for the data, wherein the at least one timeline comprises an emotional indicator for each of the plurality of segments, which indicates the determined intuitive state of the user, and output the generated timeline and at least a portion of the received data, wherein the method, which when executed by the computer further causes the computer to:

to display the timeline and sequentially display the video information, and to convert the audio information of the plurality of segments into synchronized text and symbols, wherein the audio information is divided into the plurality of segments based on pause point or based on whether a predetermined length is reached, to generate a plurality of display elements, each of the plurality of display elements comprises a respective segment from among the plurality of segments and corresponding to the converted text, and to display at least some of the generated plurality of display elements.

17. The personal emotion-based cognitive assistant system according to claim 1, wherein the at least one apparatus is a head-set comprising at least one camera in a vicinity of eyes of the user and wherein the camera captures the data comprising the synchronized visual and audio information observed by the user and wherein the synchronized visual and audio information comprises at least one of a lecture observed by the user, an element of an activity undertaken by the user, and equipment manipulated by the user.

18. A personal emotion-based cognitive assistant system comprising:

a headset, worn by a user, comprising:

at least one camera configured to capture an environment of the user, which comprises visual data viewed by the user in synchronization with audio data heard by the user, a plurality of sensors, positioned at predetermined locations on a band of the headset, configured to capture emotional state of the user synchronized with the data captured by the at least one camera, a first processor configured to process the captured emotion state of the user and the captured environment of the user and to generate a plurality of data segments, and a transmitter configured to transmit the generated plurality of data segments to an external device; and a review apparatus comprising a memory and a second processor, wherein the second processor is configured to:

receive the plurality of data segments;

for each of the plurality of data segments, determine an intuitive state of the user, comprising a type of correlations and a level of correlations, generated from a comparison between predetermined components of the emotional state of the user, which corresponds to the respective data segment, from among the plurality of data segments, and distinctive reference signals stored in the memory, wherein the distinctive reference signals represent distinctive intuitive reference samples, generate at least one timeline, and control to display the generated timeline comprising an emotional indicator for each of the plurality of segments, wherein the emotional indicator indicates the determined intuitive state of the user, wherein the review apparatus further comprises:

a display configured to display the timeline and sequentially display the video information, and a speech to text converter configured to convert the audio information of the plurality of segments into synchronized text and symbols, wherein the audio information is divided into the plurality of segments based on pause point or based on whether a predetermined length is reached, wherein the second processor generates a plurality of display elements, each of the plurality of display elements comprises a respective segment from among the plurality of segments and corresponding text converted by the speech to text converter, and wherein the display is further configured to display at least some of the generated plurality of display elements.

19. The personal emotion-based cognitive assistant system according to claim 18, wherein the review apparatus is the external apparatus and wherein each of the plurality of sensors capture an activity of a particular portion of a brain of the user based on a predetermined location of the respective sensor and output a signal indicative of the active of the respective particular portion of the brain and wherein the first processor generates the captured emotional state of the user based on a plurality of signals output by the plurality of sensors.

* * * * *